United States Patent
Yang et al.

(10) Patent No.: US 11,332,770 B2
(45) Date of Patent: May 17, 2022

(54) METHOD FOR PREPARING TRANSFRUCTOSYLATED STEVIOL GLYCOSIDE USING MICROORGANISM OF GENUS ARTHROBACTER

(71) Applicant: CJ Cheiljedang Corporation, Seoul (KR)

(72) Inventors: Tae Joo Yang, Seoul (KR); In Sung Kang, Seoul (KR); Min Hoe Kim, Seoul (KR); Sunghee Park, Seoul (KR); Sun Chu, Seoul (KR); Seong Bo Kim, Seoul (KR); Young Mi Lee, Seoul (KR); Young Su Lee, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 13 days.

(21) Appl. No.: 16/759,437

(22) PCT Filed: Oct. 25, 2018

(86) PCT No.: PCT/KR2018/012766
§ 371 (c)(1),
(2) Date: Apr. 27, 2020

(87) PCT Pub. No.: WO2019/083309
PCT Pub. Date: May 2, 2019

(65) Prior Publication Data
US 2020/0291443 A1    Sep. 17, 2020

(30) Foreign Application Priority Data
Oct. 27, 2017 (KR) .................. 10-2017-0140846

(51) Int. Cl.
*C12P 19/56* (2006.01)
*C07H 15/24* (2006.01)

(52) U.S. Cl.
CPC .............. *C12P 19/56* (2013.01); *C07H 15/24* (2013.01)

(58) Field of Classification Search
CPC .......... C12P 19/56; C12P 19/18; C07H 15/24; C07H 15/256; A23L 33/135; A23L 27/36
See application file for complete search history.

(56) References Cited

FOREIGN PATENT DOCUMENTS

| | | | | |
|---|---|---|---|---|
| JP | 04-293494 A | | 10/1992 | |
| JP | 05-077675 | * | 10/1993 | ........... C07H 15/256 |
| JP | 05-077675 B2 | | 10/1993 | |
| JP | H05-77675 B2 | | 10/1993 | |
| KR | 10-1991-0020769 A | | 11/1991 | |
| KR | 10-1995-0002868 | * | 3/1995 | .............. C12P 19/56 |
| KR | 10-1995-0002868 B1 | | 3/1995 | |
| WO | 2017/093895 A1 | | 6/2017 | |

OTHER PUBLICATIONS

Chaturvedula et al., Two Minor Diterpene Glycosides from the Leaves of Stevia rebaudiana. Natural Product Communications, 2011, vol. 6(2): 175-178. (Year: 2011).*
Purkayastha et al., Steviol glycosides in purified stevia leaf extract sharing the same metabolic fate. Regulatory Toxicology and Pharmacology 2016, vol. 77: 125-133. (Year: 2016).*
Spohner et al., Enzymatic production of prebiotic fructo-oligosteviol glycosides. Journal of Molecular Catalysis B: Enzymatic 2016, vol. 131:79-84. (Year: 2016).*
Win et al., Enzymatic synthesis of two novel non-reducing oligosaccharides using transfructosylation activity with β-fructofuranosidase from Arthrobacter globiformis. Biotechnology Letters 26: 499-503, 2004. (Year: 2004).*
Extended European Search Report issued in corresponding European Patent Application No. 18869679.3 dated Jul. 2, 2021.
Ishikawa et al., "Production of Stevioside and Rubusoside Derivatives by Transfructosylation of beta-Fructofuranosidase," Agricultural and Biological Chemistry, 54 (12): 3137-3143 (1990).
Xu et al., "Production of beta-Fructofuranosidase by *Arthrobacter* sp. and Its Application in the Modification of Stevioside and Rebaudioside A," Food Technology and Biotechnology, 42 (2): 137-143 (2009).
International Search Report issued in corresponding International Patent Application No. PCT/KR2018/012766 dated May 8, 2019.

* cited by examiner

*Primary Examiner* — Ganapathirama Raghu
(74) *Attorney, Agent, or Firm* — Morgan, Lewis & Bockius LLP

(57) ABSTRACT

The present disclosure relates to a method for preparing a transfructosylated steviol glycoside using *Arthrobacter*-derived microorganisms, a culture thereof, a supernatant of the culture, an extract of the culture, and a lysate of the microorganisms.

13 Claims, 26 Drawing Sheets
Specification includes a Sequence Listing.

[Fig. 1a]
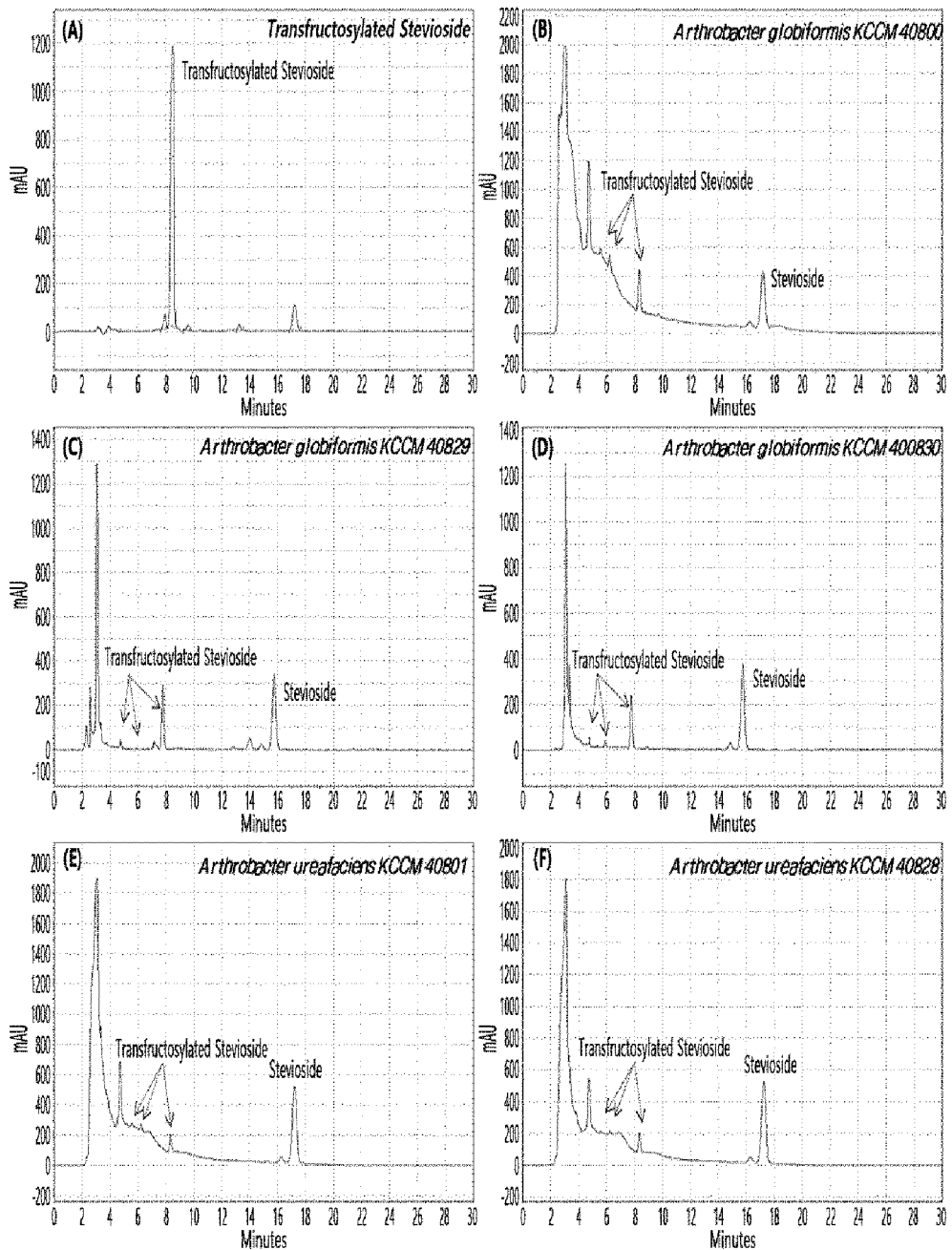

[Fig. 1b]
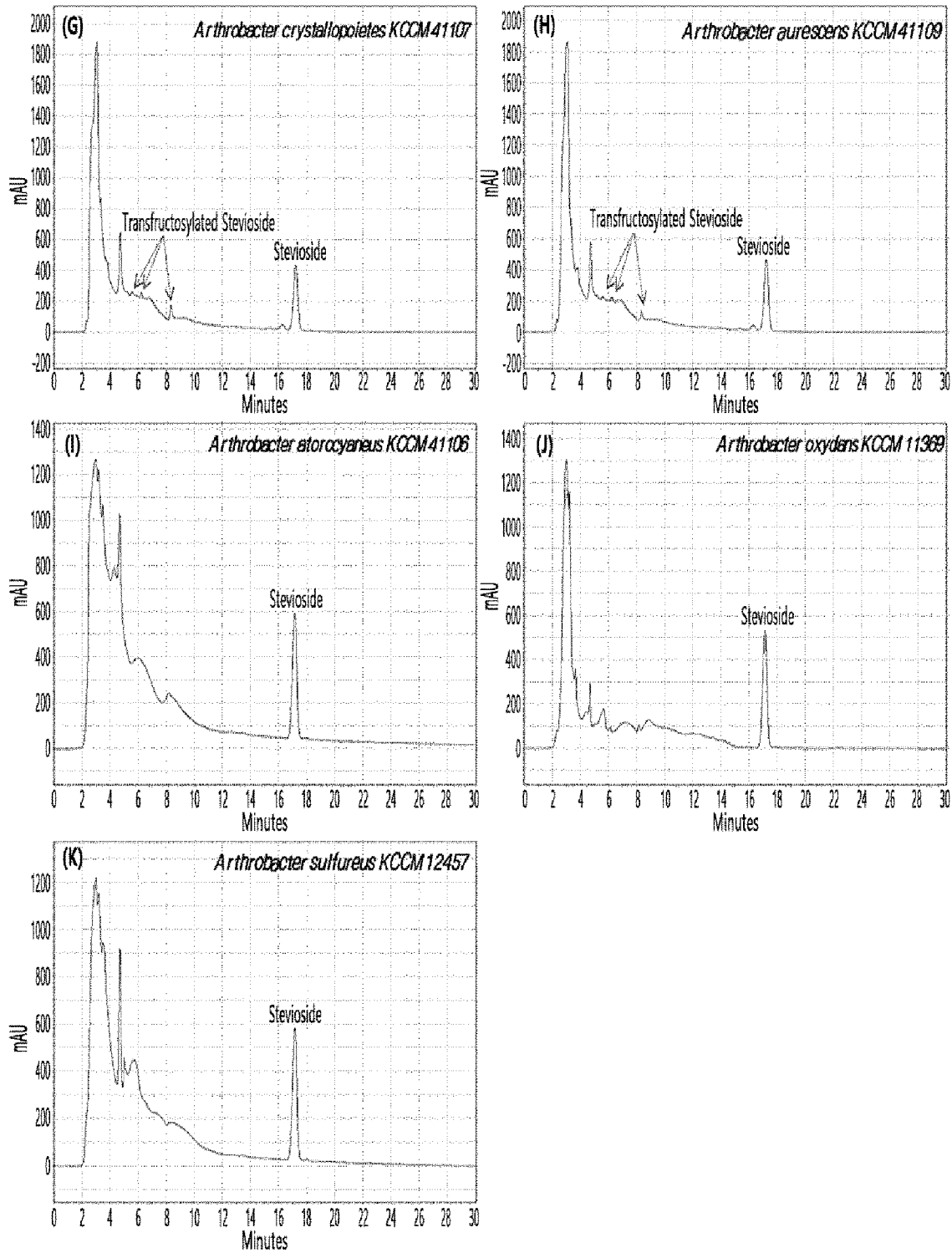

[Fig. 2a]
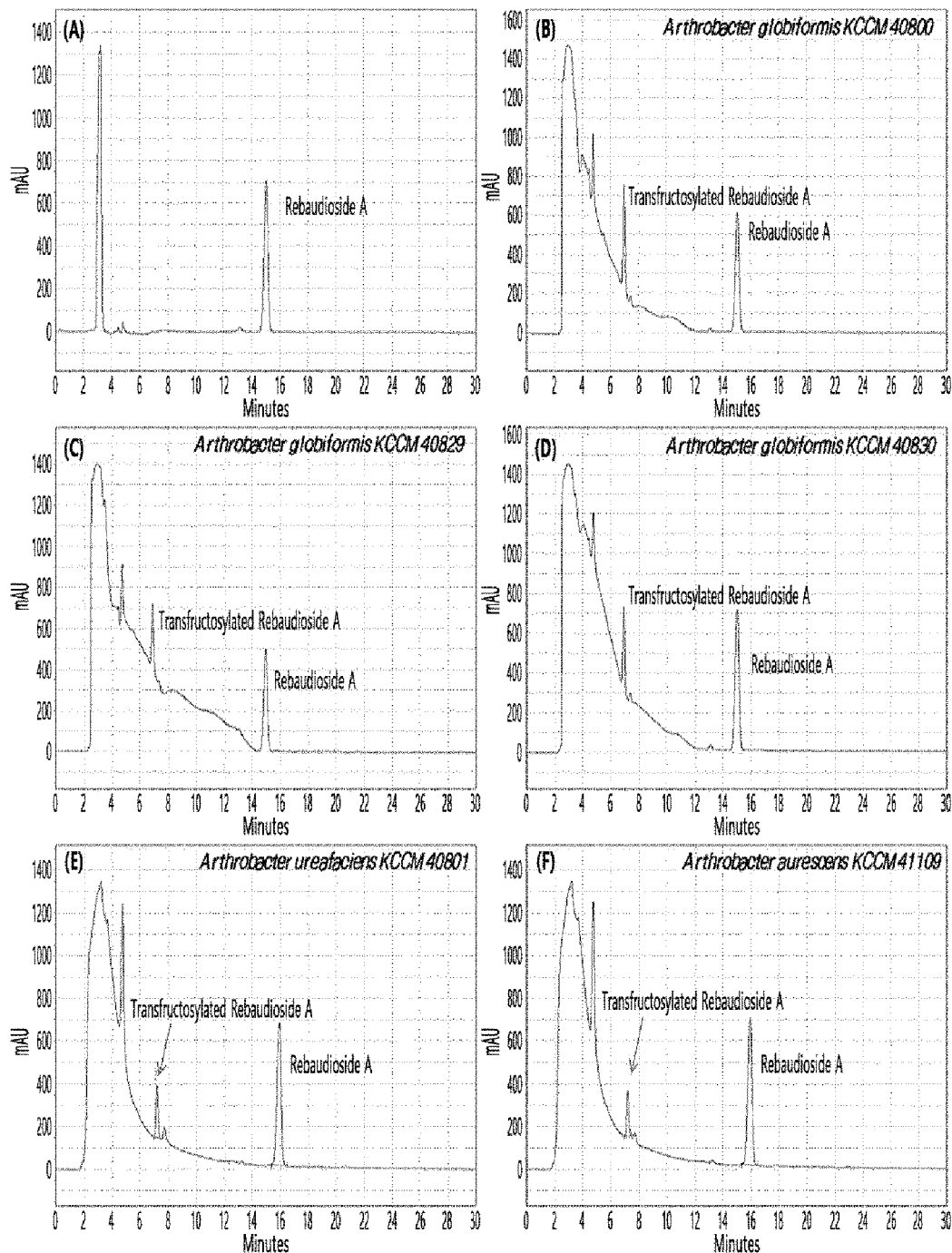

[Fig. 2b]
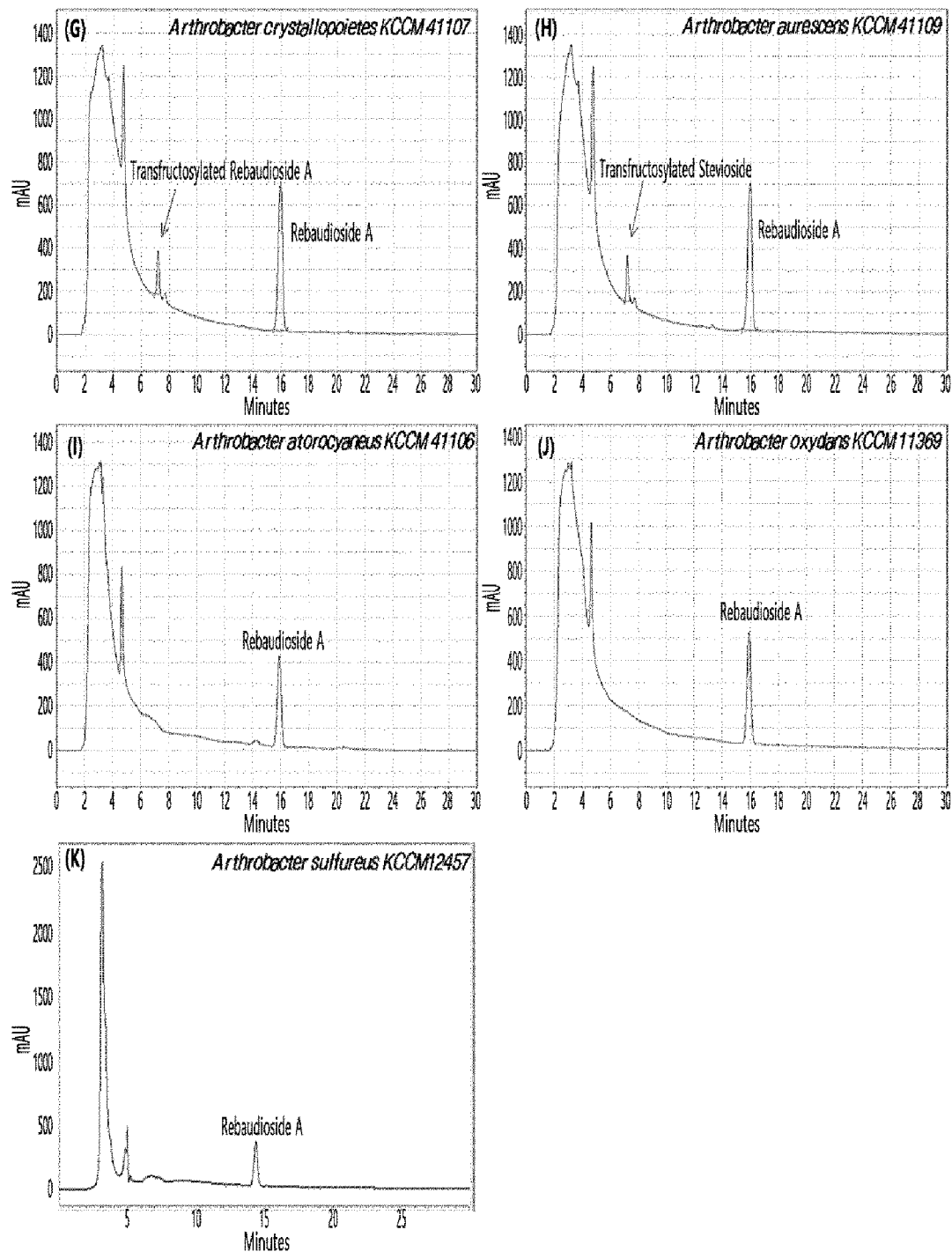

[Fig. 3a]
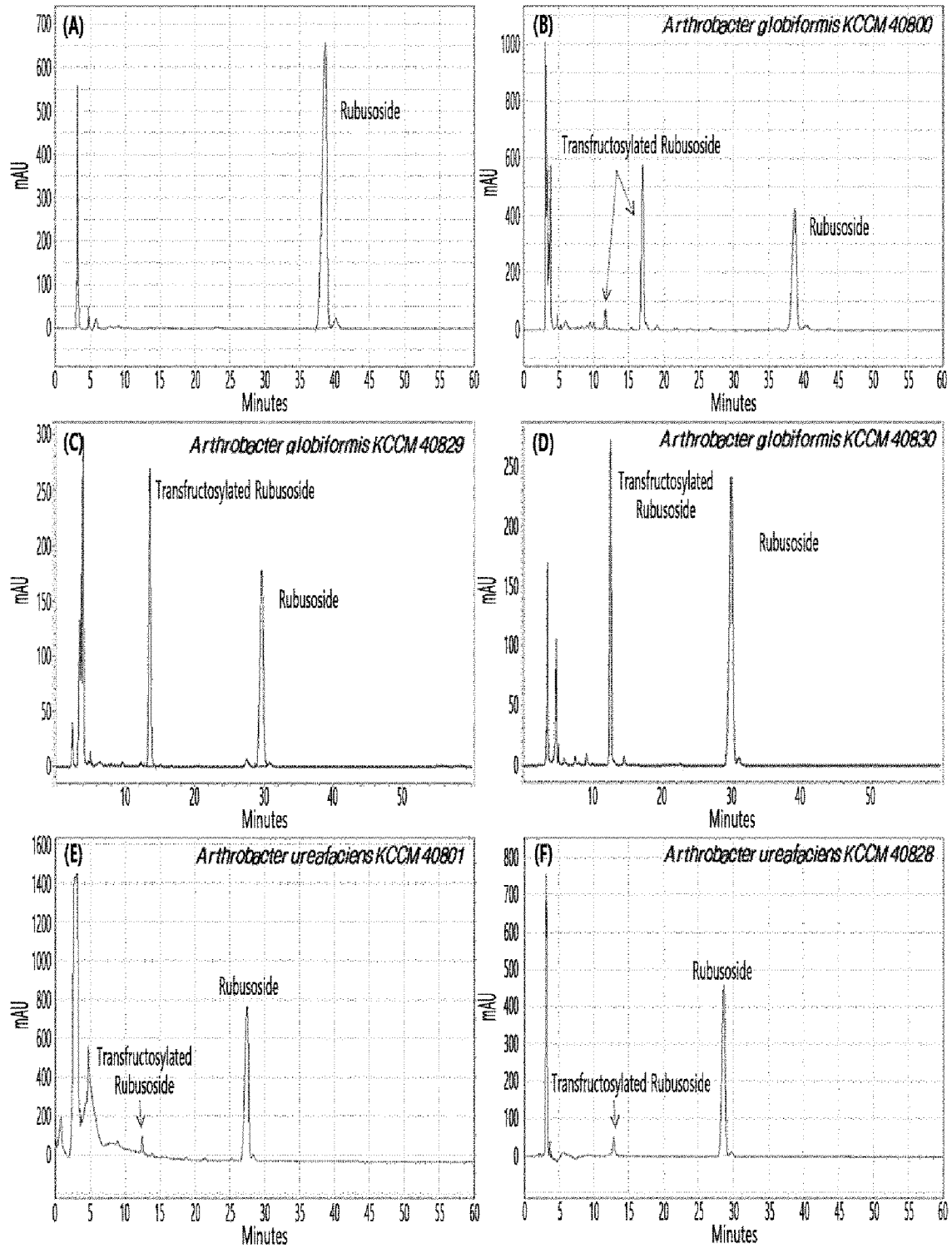

[Fig. 3b]
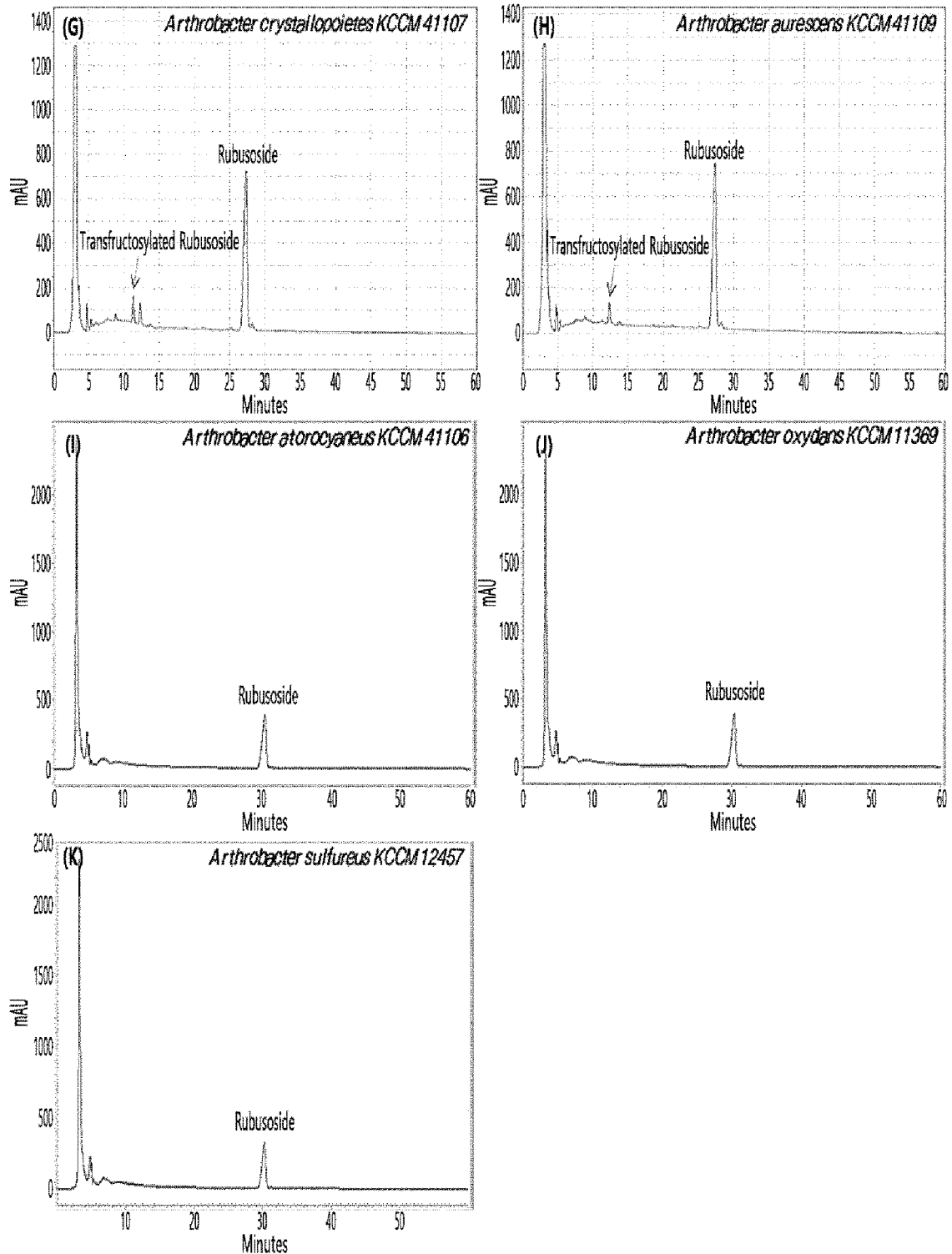

[Fig. 4a]
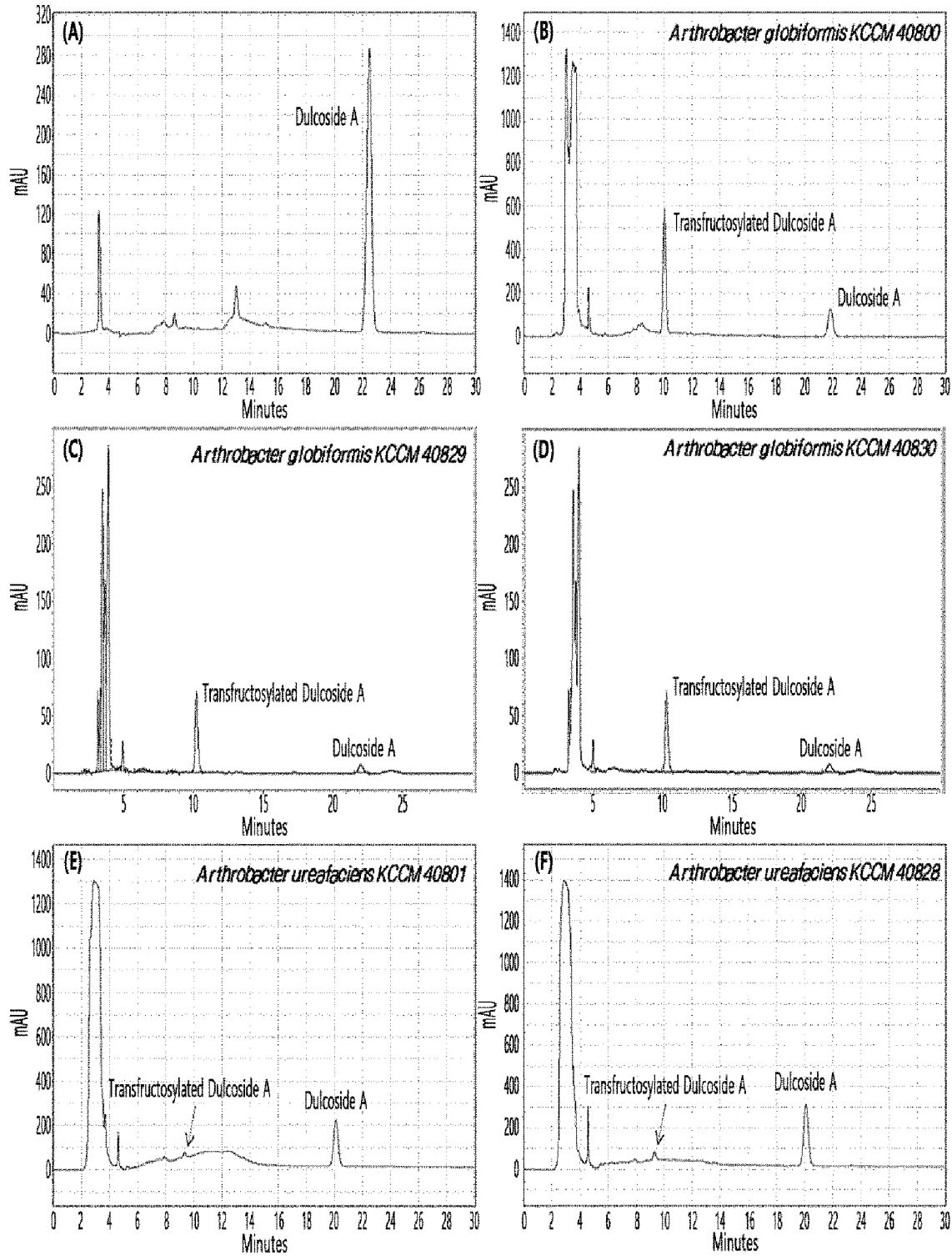

[Fig. 4b]
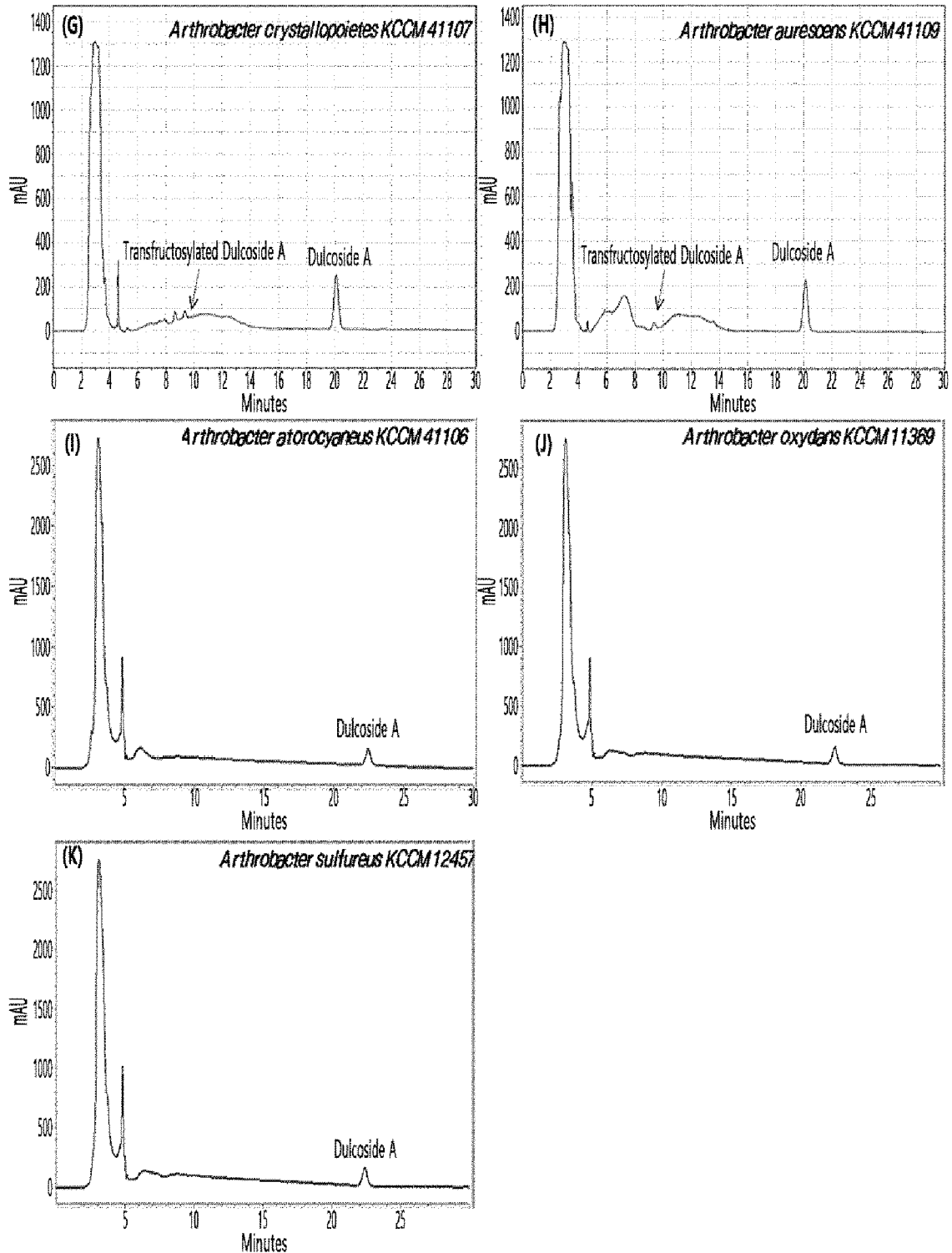

[Fig. 5a]
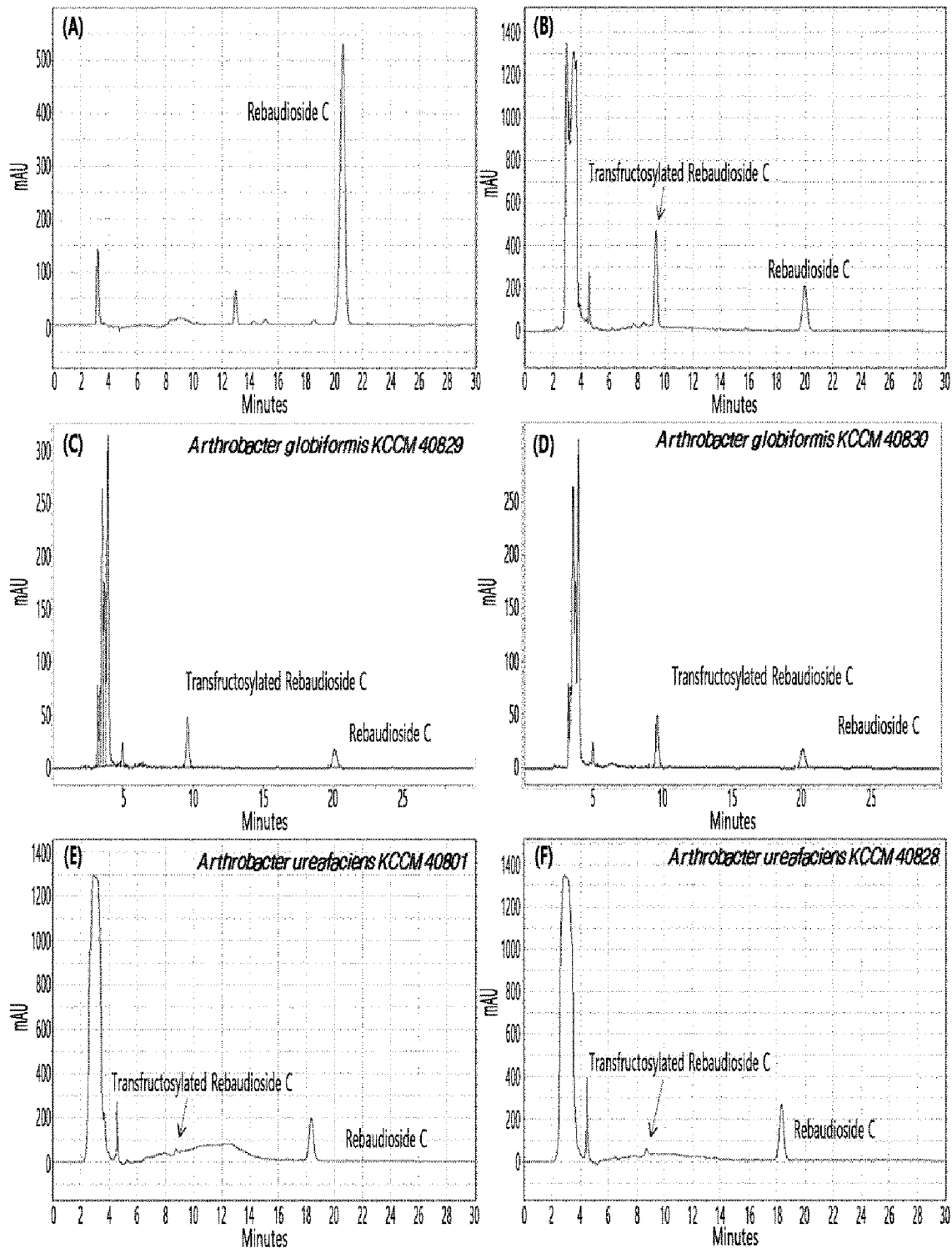

[Fig. 5b]
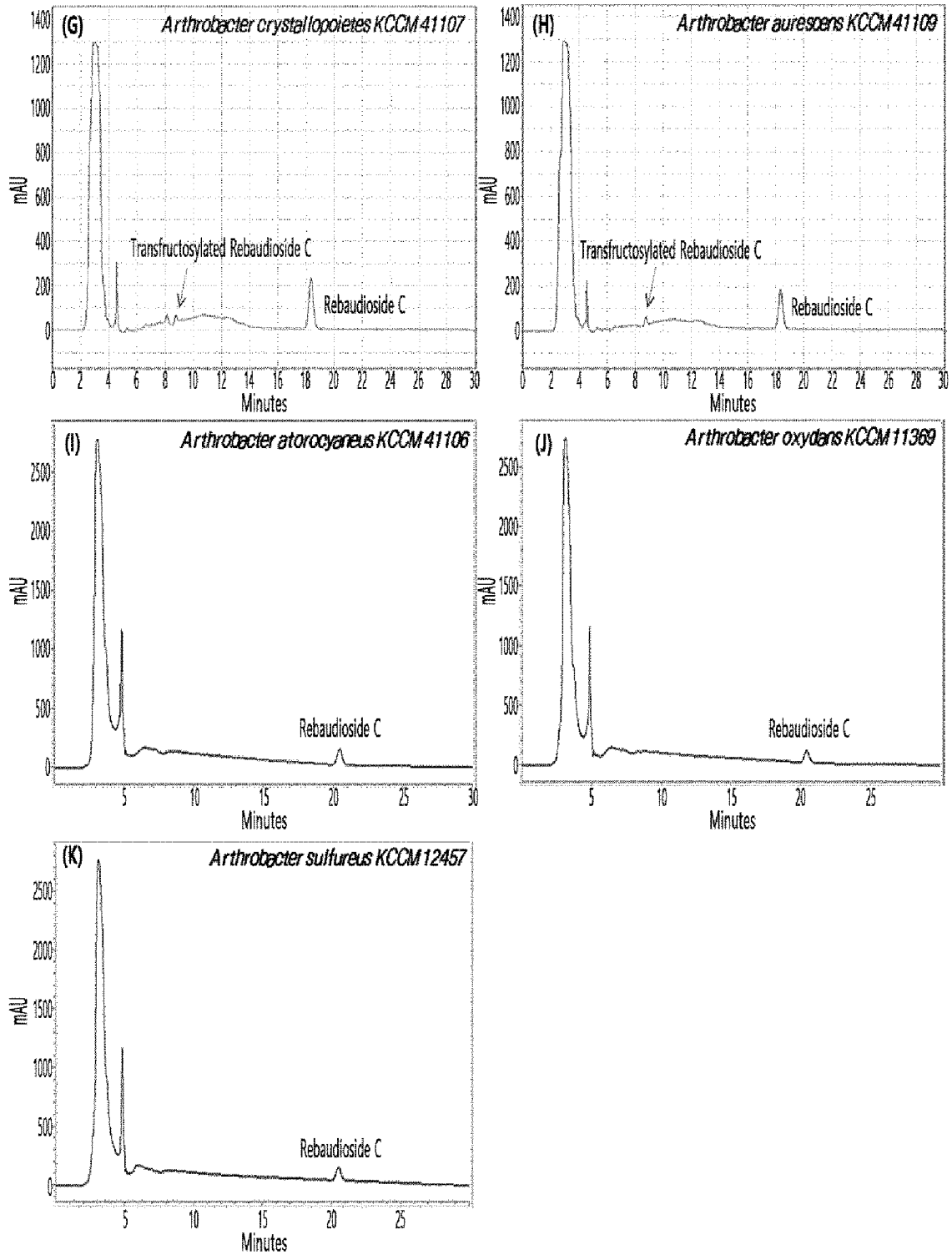

[Fig. 6a]
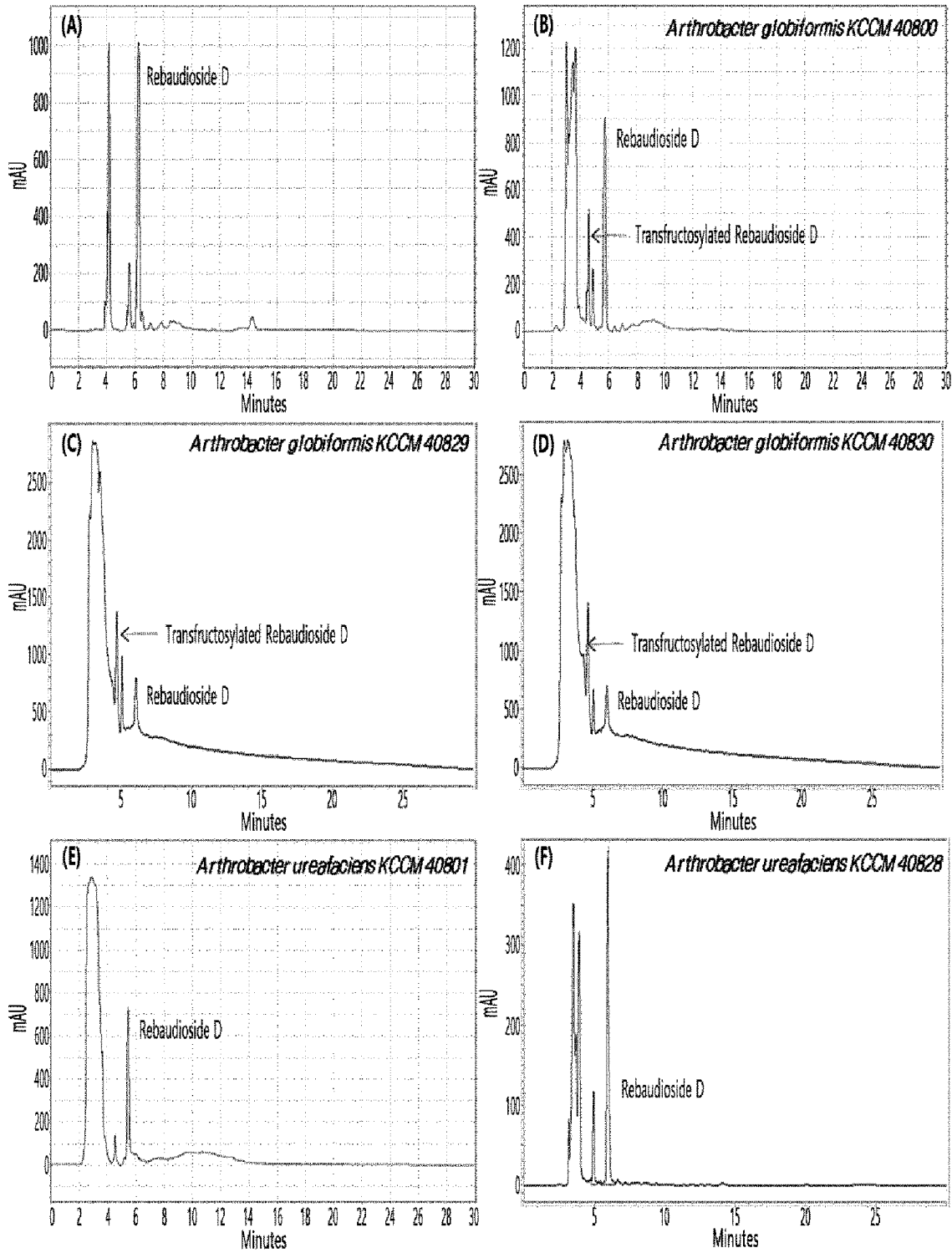

[Fig. 6b]
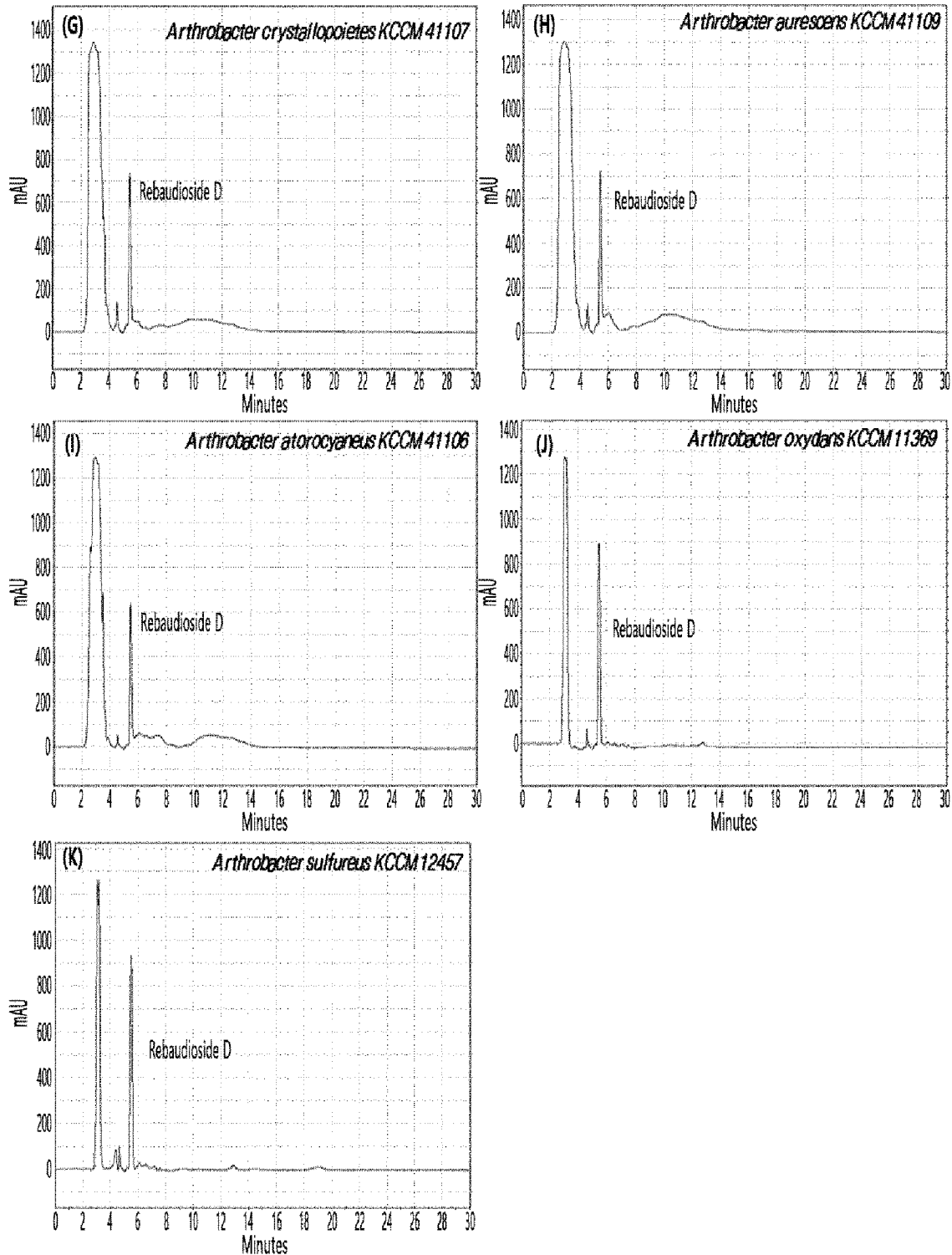

[Fig. 7a]
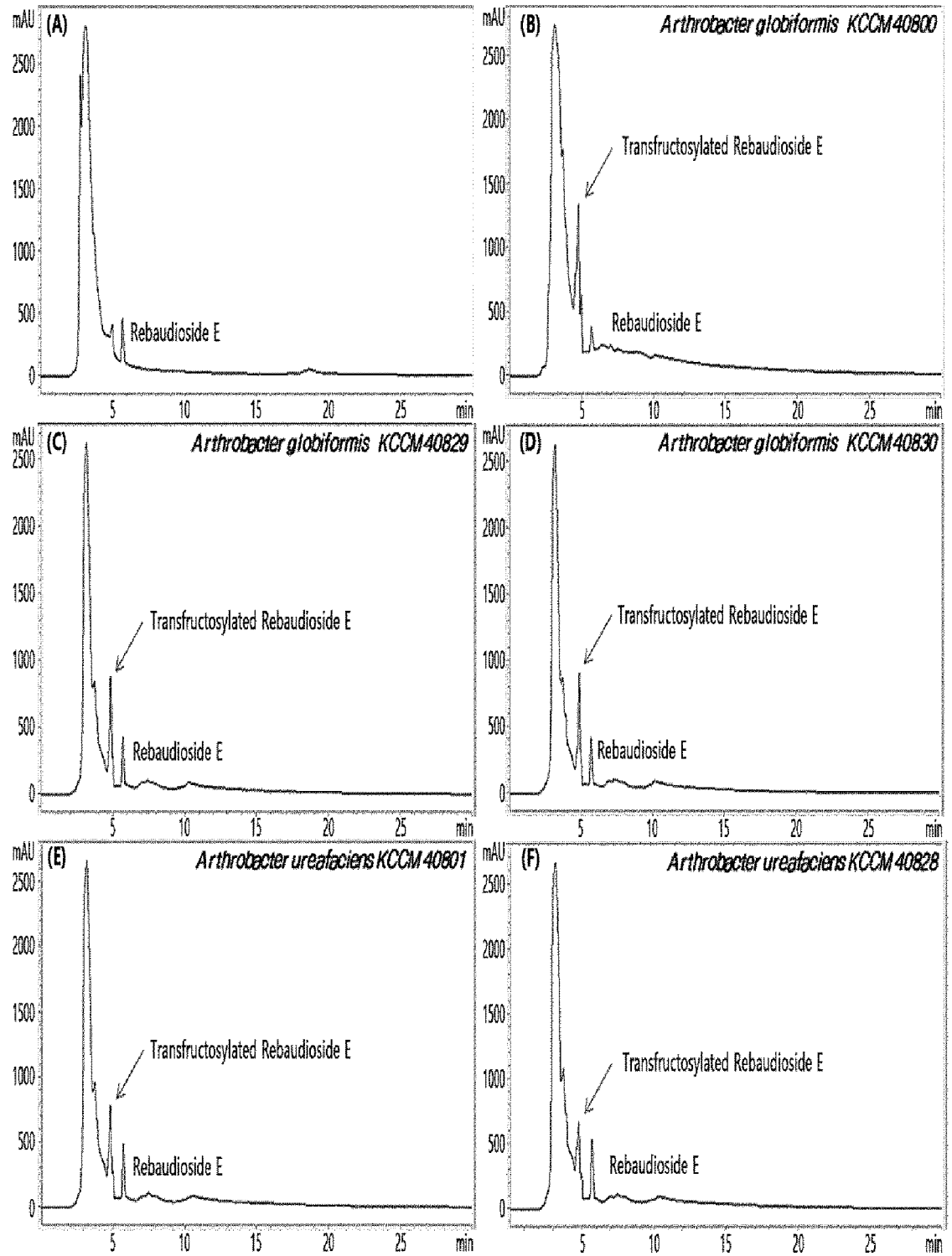

[Fig. 7b]
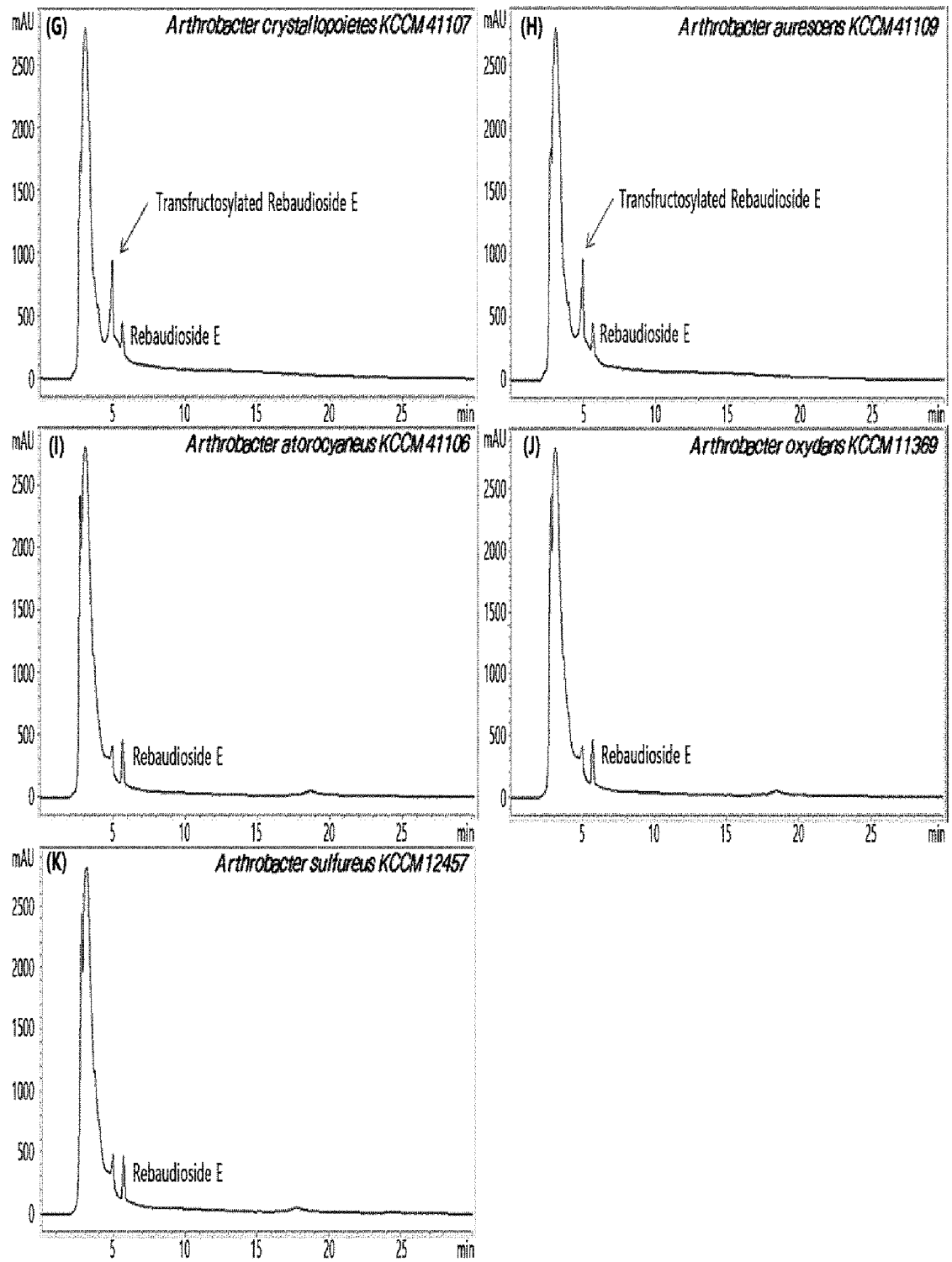

[Fig. 8a]
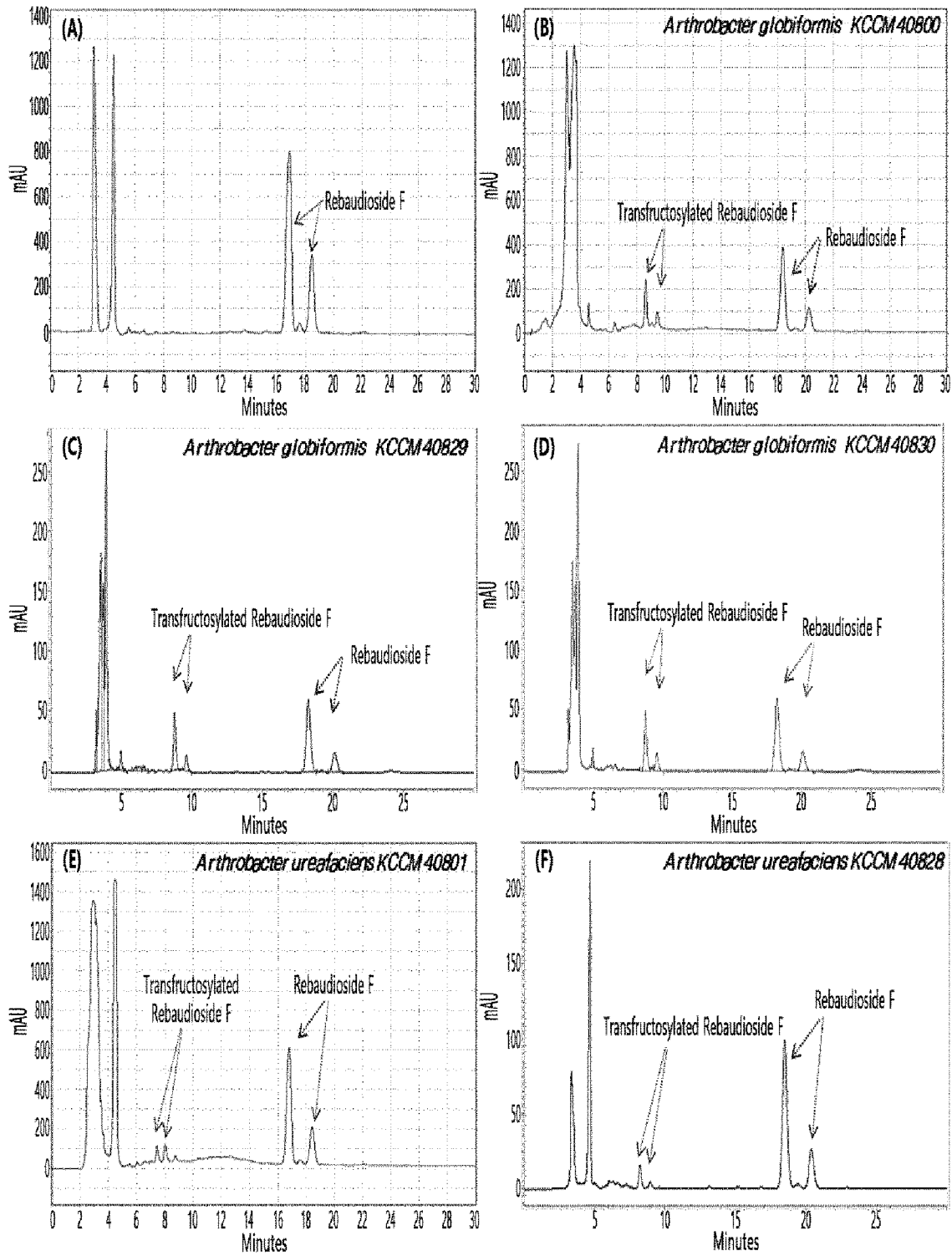

[Fig. 8b]
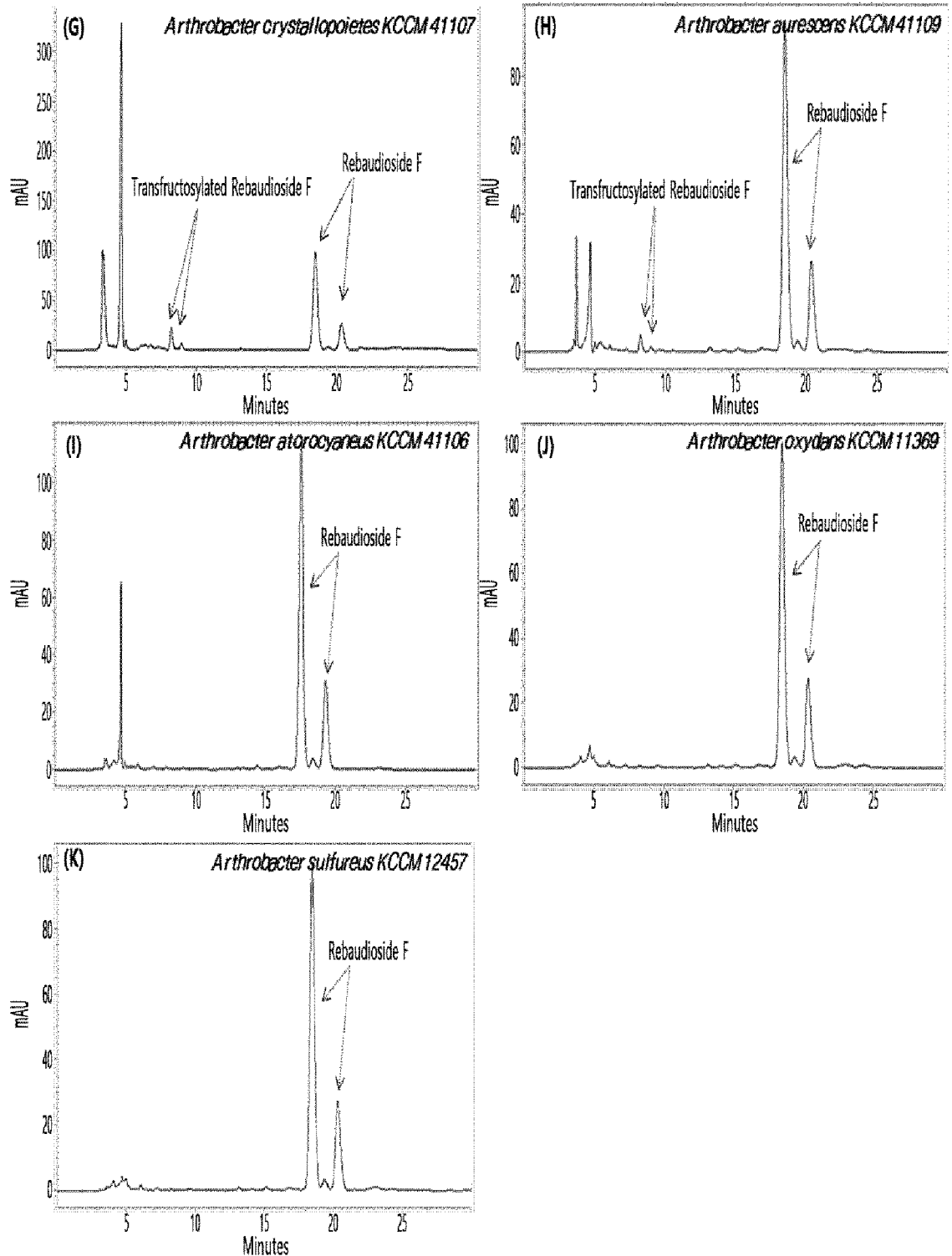

[Fig. 9a]
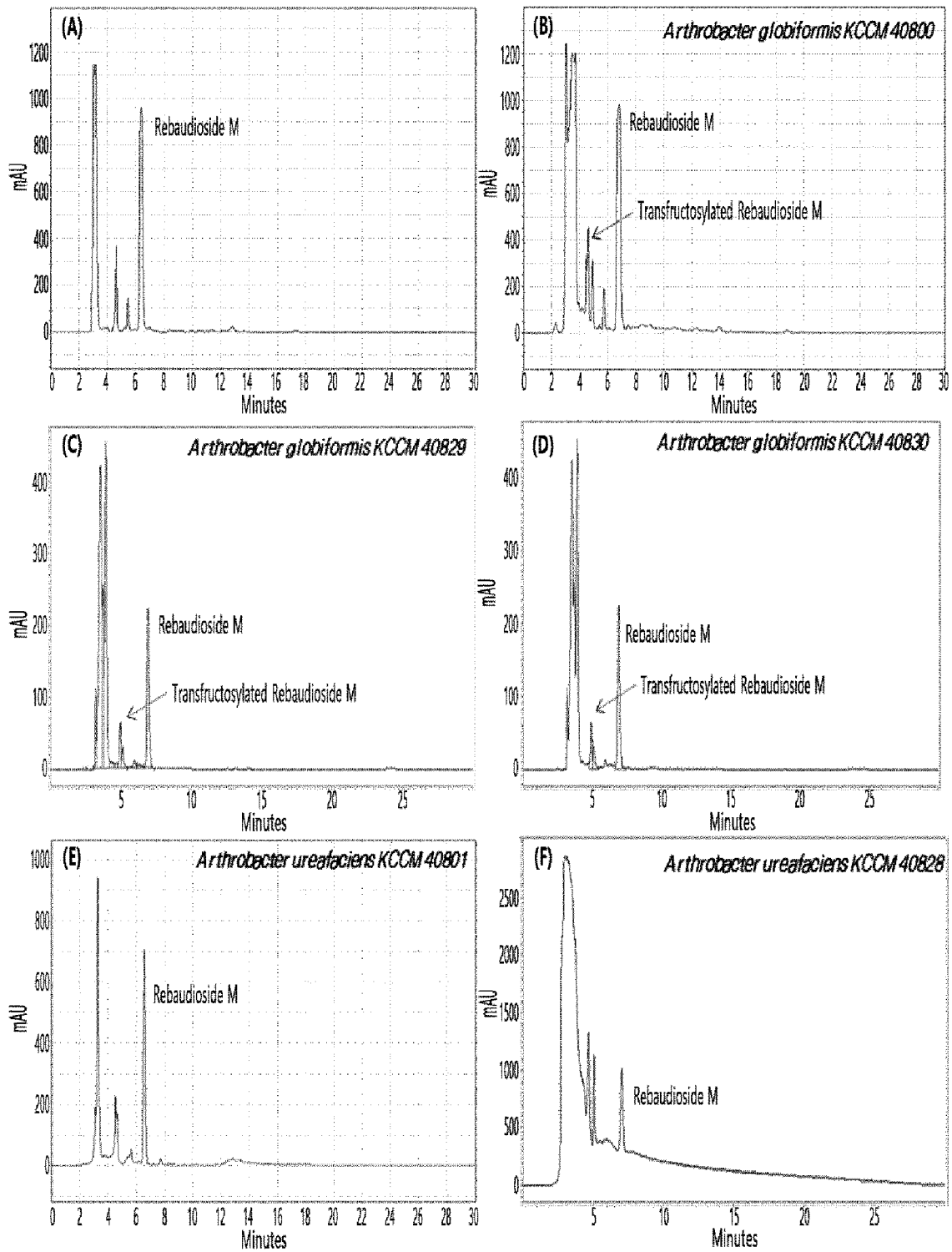

[Fig. 9b]
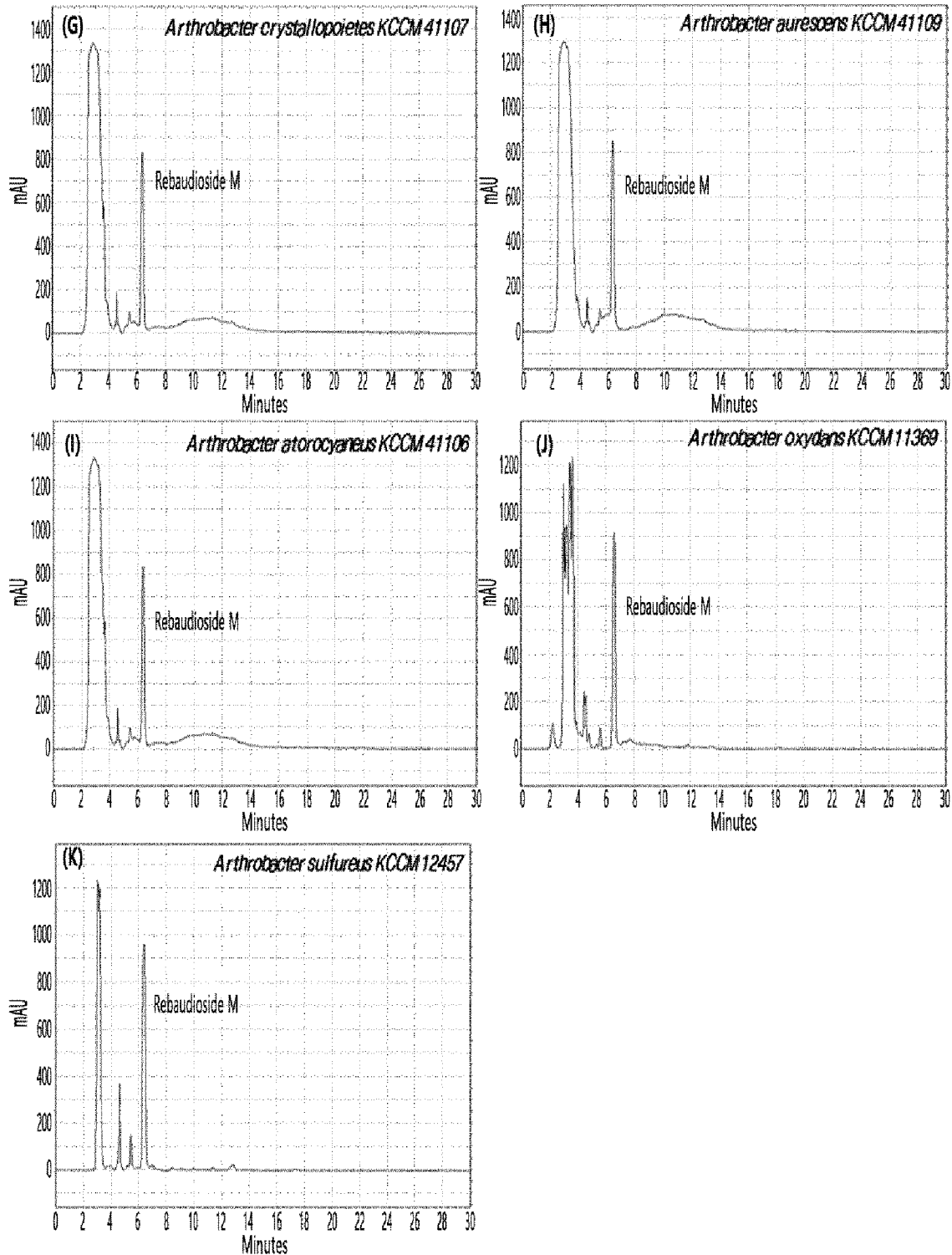

[Fig. 10a]
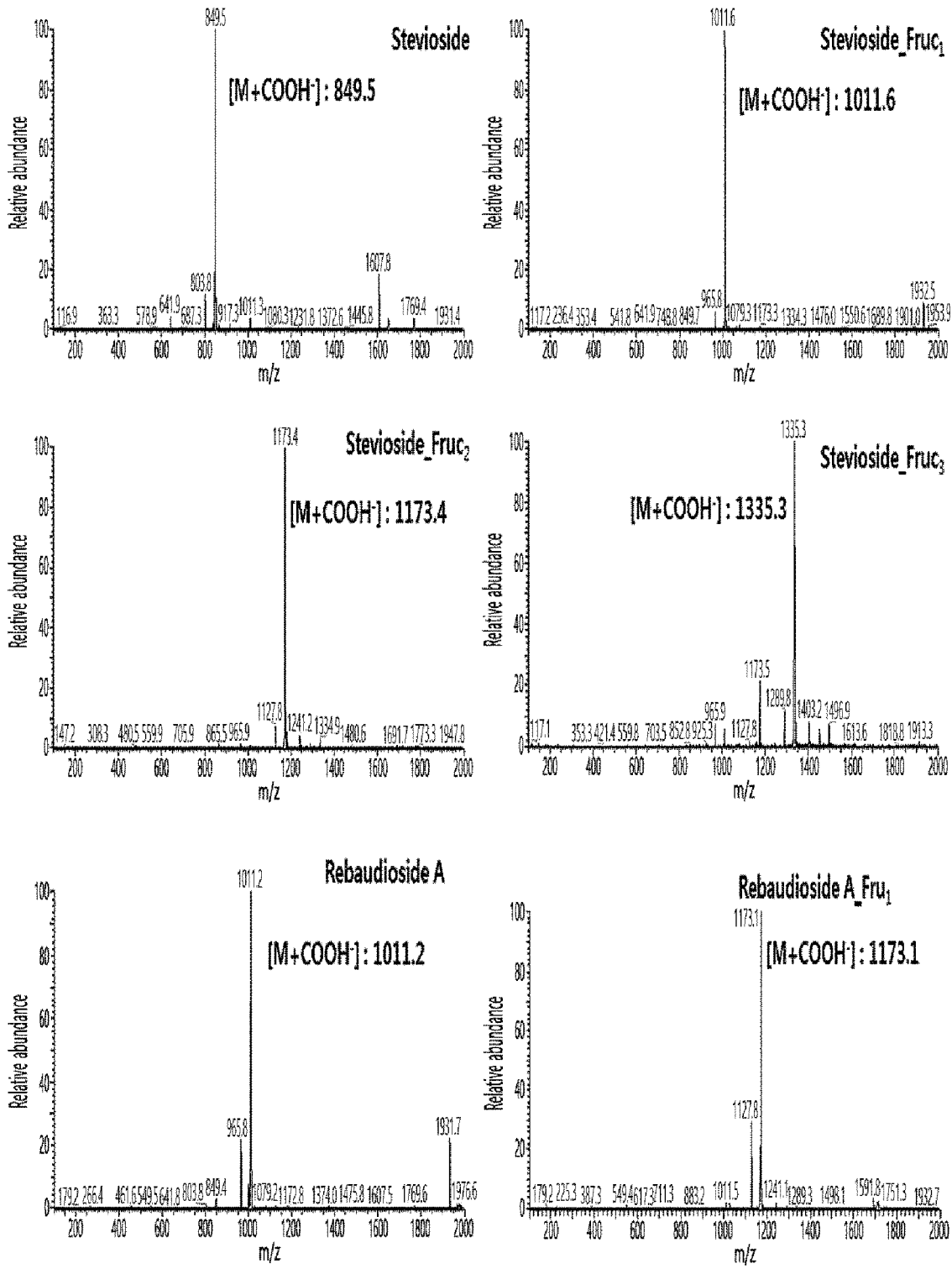

[Fig. 10b]
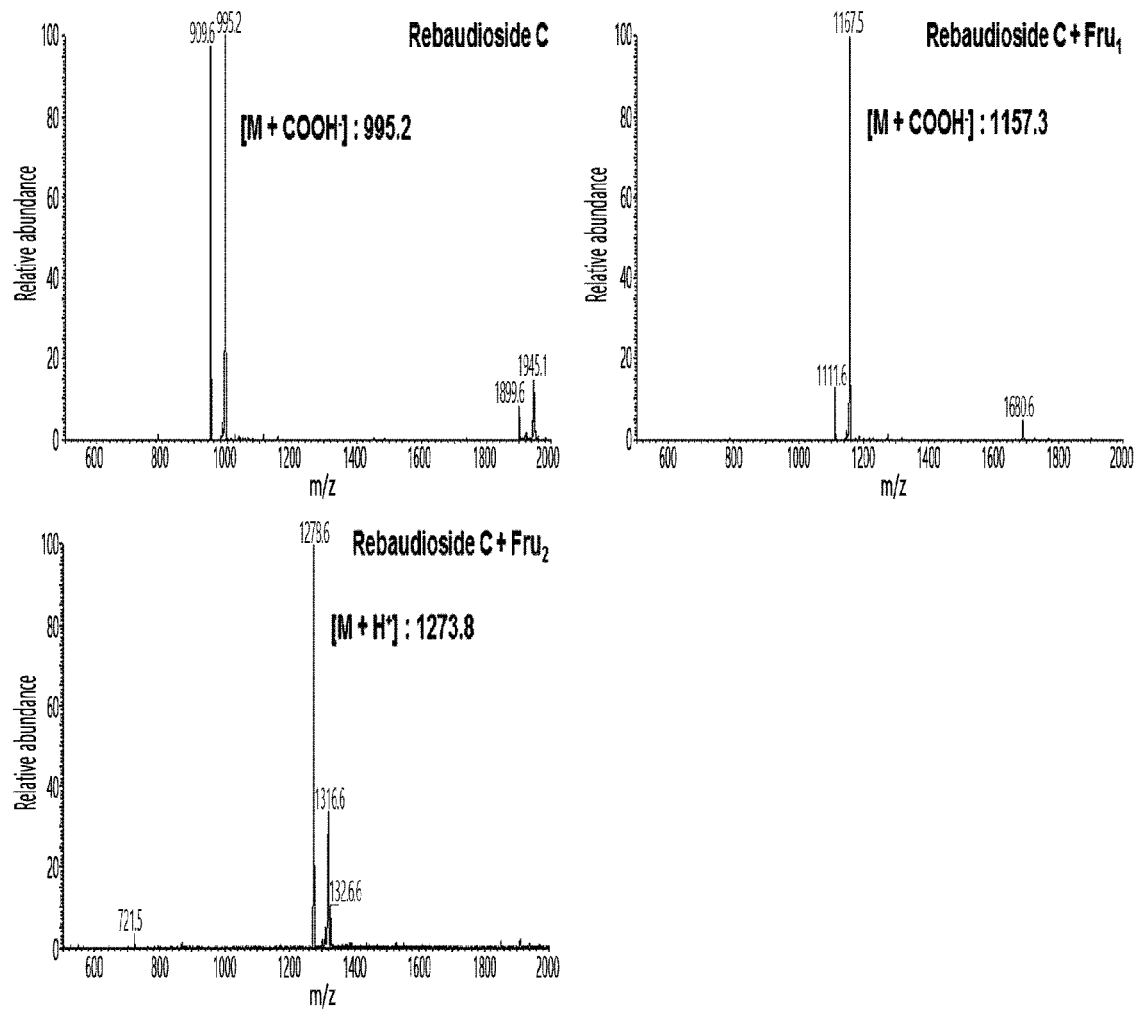

[Fig. 10c]
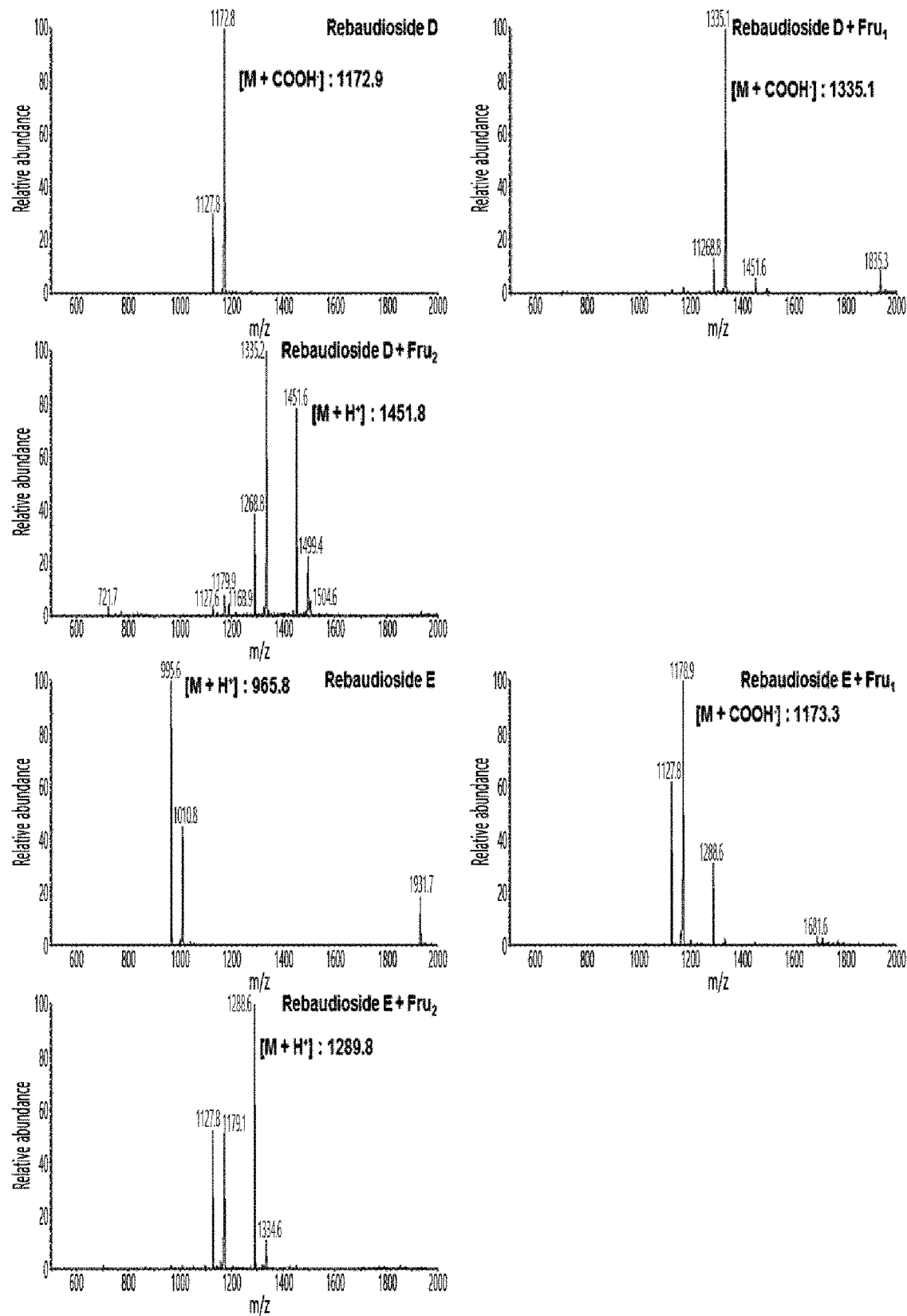

[Fig. 10d]
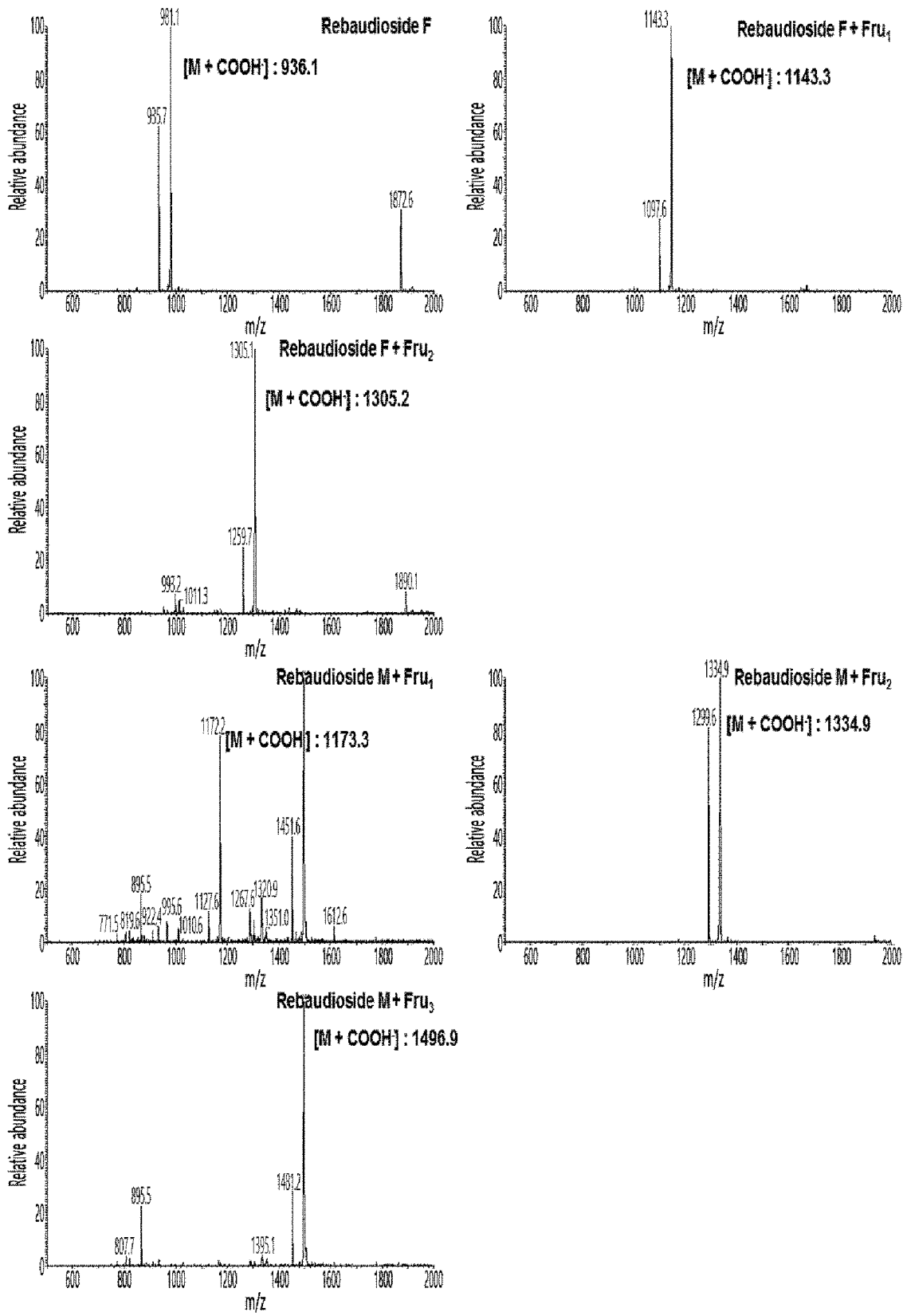

[Fig. 10e]
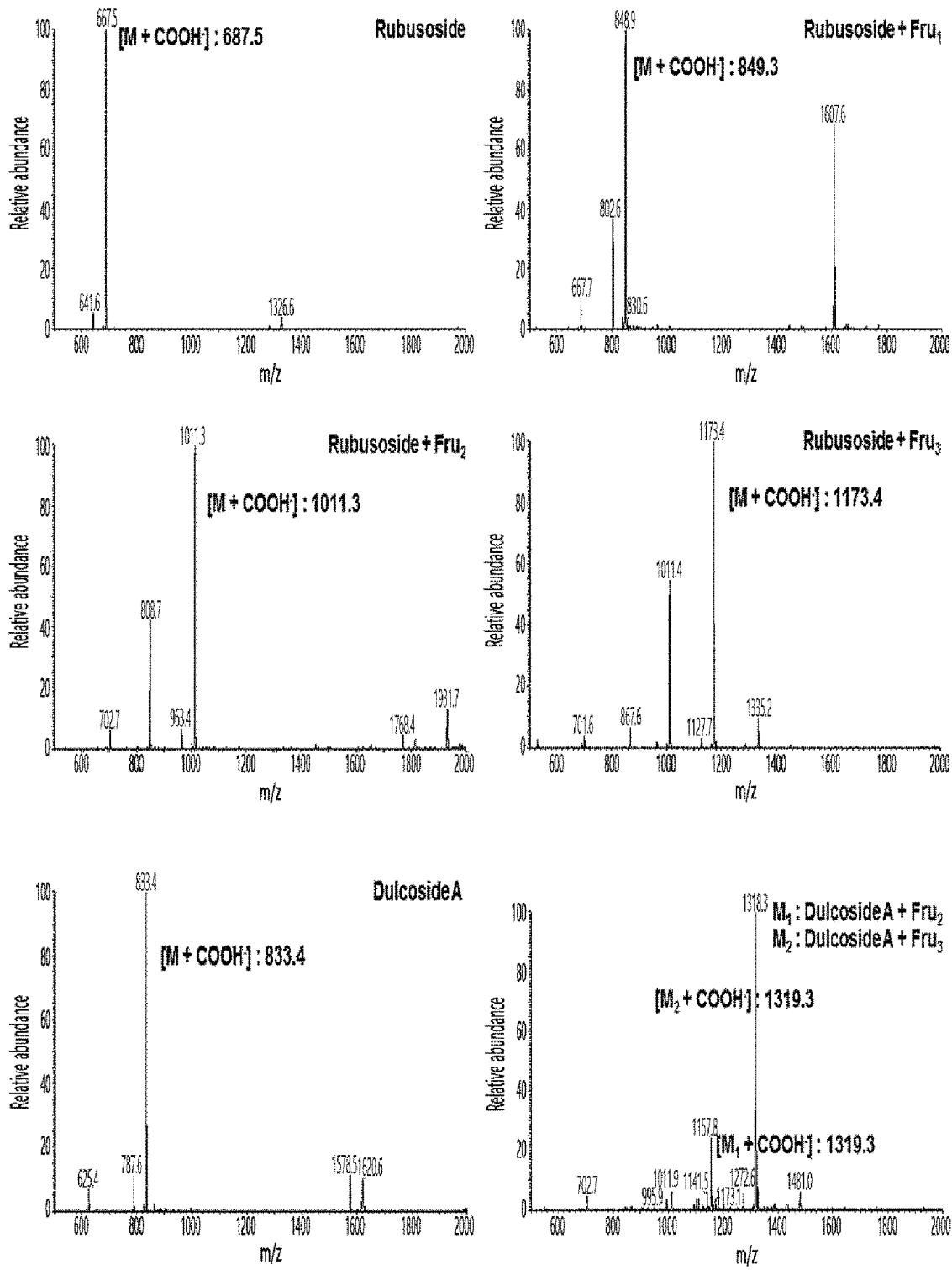

[Fig. 11]
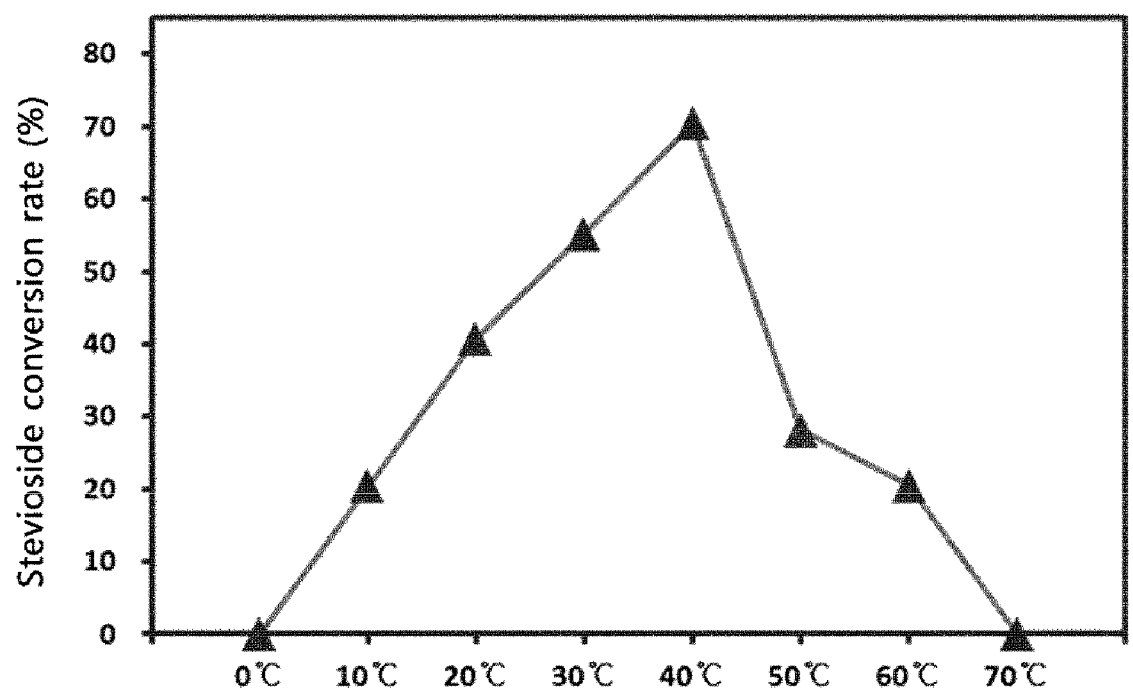
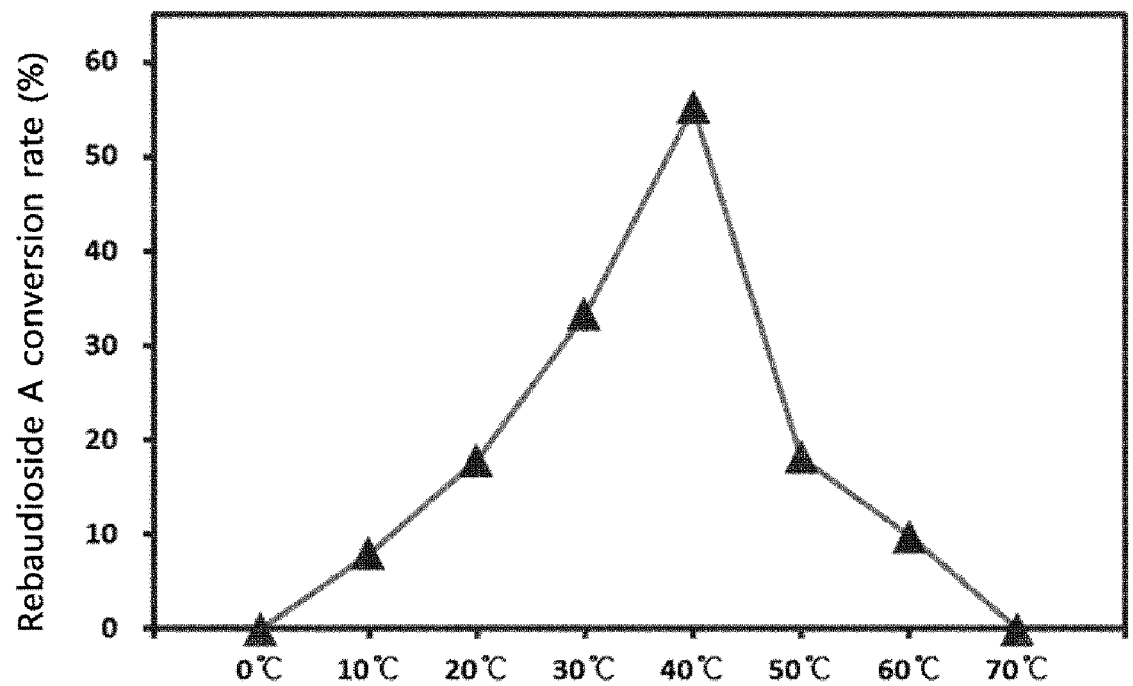

[Fig. 12]
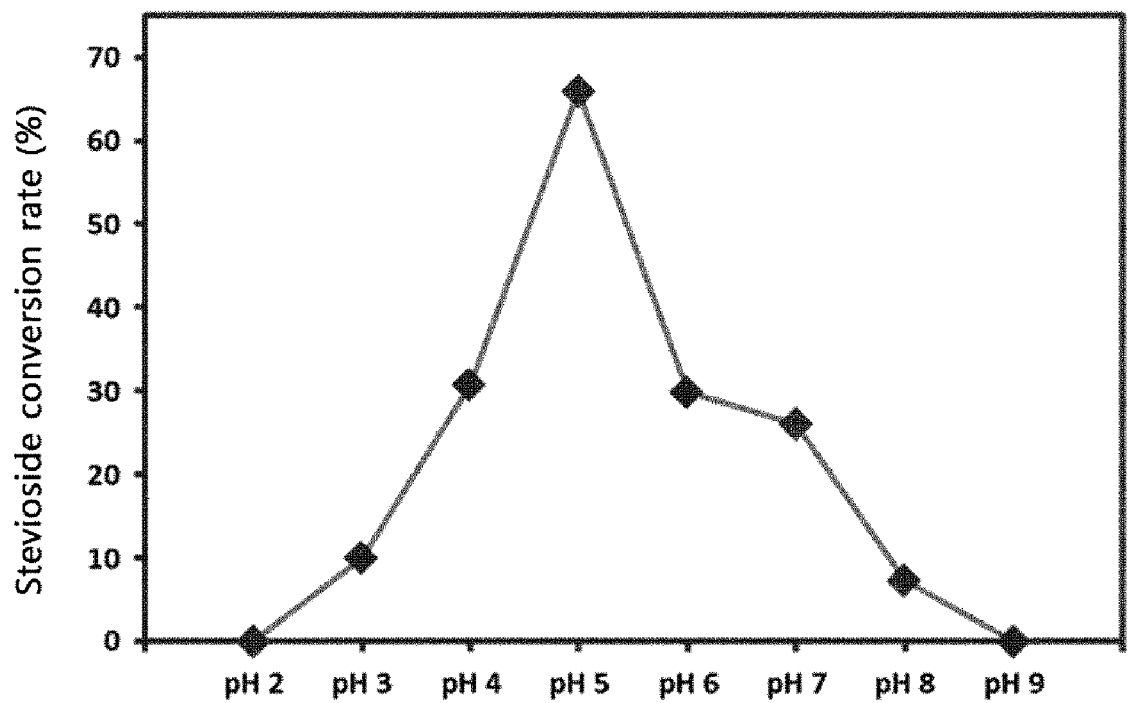
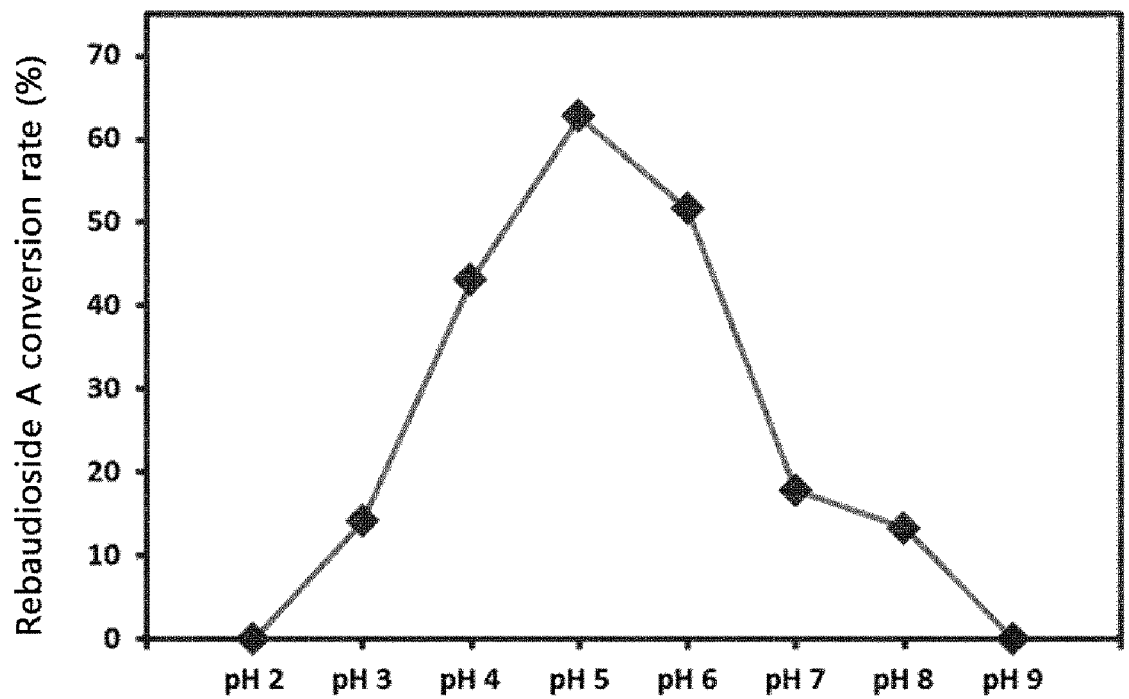

[Fig. 13]
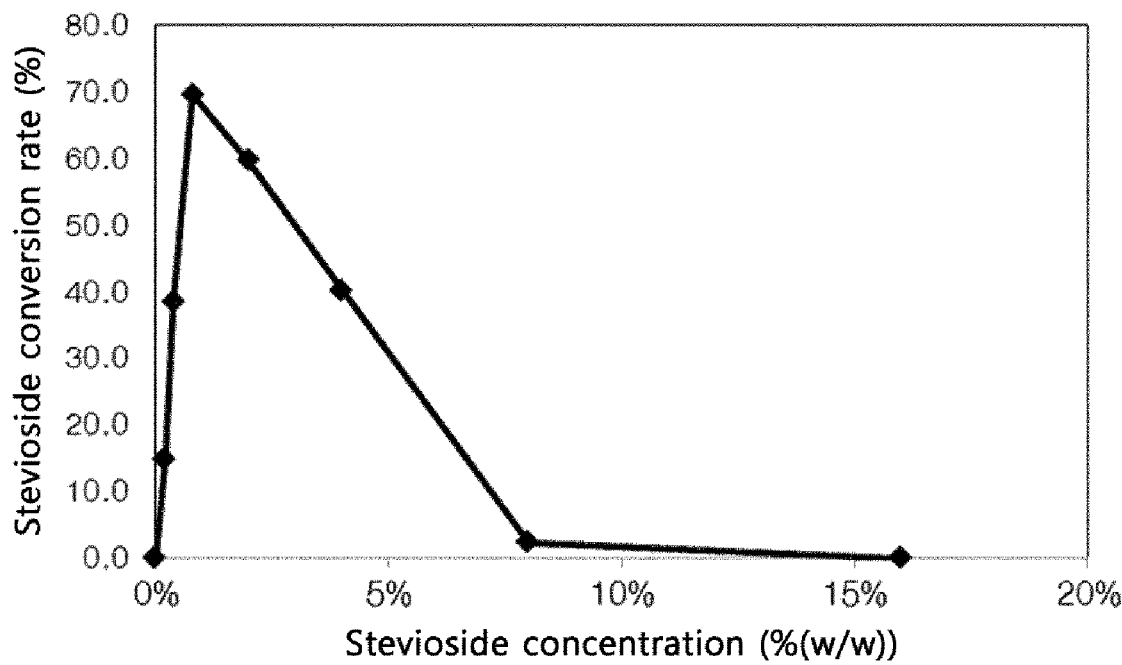
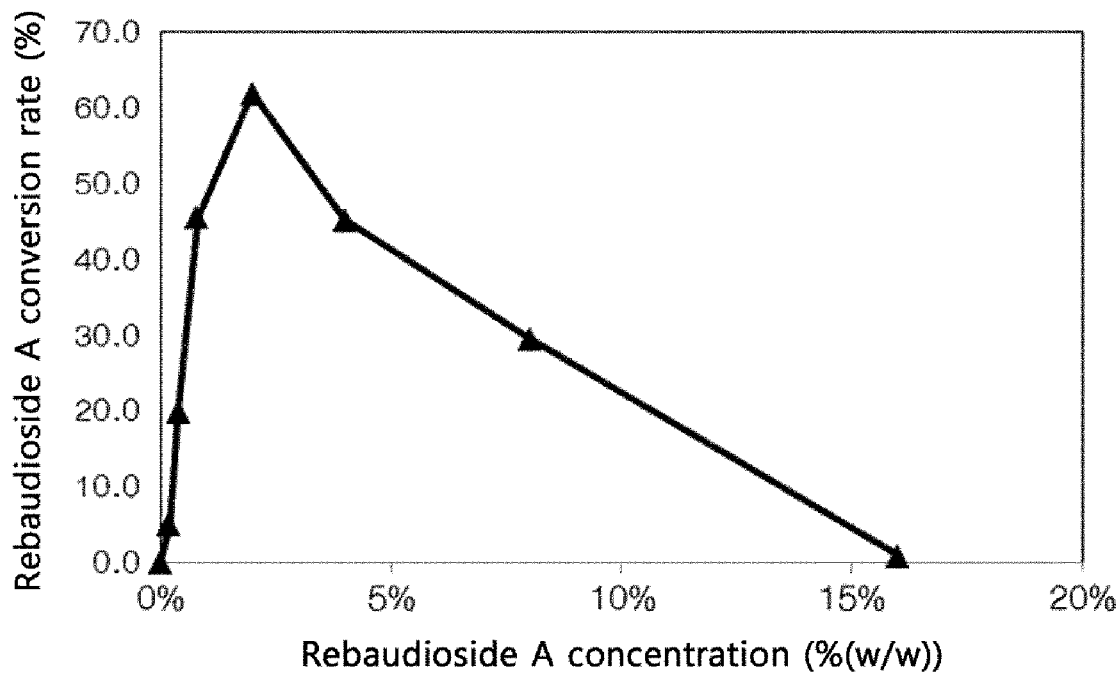

SEQUENCE LISTING

<160> NUMBER OF SEQ ID NOS: 2

<210> SEQ ID NO 1
<211> LENGTH: 419
<212> TYPE: PRT
<213> ORGANISM: Unknown
<220> FEATURE:
<223> OTHER INFORMATION: Arthrobacter globiformis beta-
      fructofuranosidase protein

<400> SEQUENCE: 1

Met Arg Thr Cys Thr Val Arg Ala Val Arg His Arg Thr Val Asn Lys
1               5                   10                  15

Arg Thr Lys Arg Gly Thr Ala Ala Ser Gly Ala Gly Ala Thr Ser Gly
            20                  25                  30

Ala Val Ala Ala Thr Asp Ala Ala Gly Thr His Thr Lys Ala Tyr Ser
        35                  40                  45

Thr Asp Asn Thr Ser Arg Trp Thr Arg Ala Asp Ala Lys Lys Ala Met
    50                  55                  60

Ser Asp Ala Gly Ser Arg Asn Ser Met Thr Tyr Thr Met Thr Val
65                  70                  75                  80

Ser Asp Asp Met Ser Asn Lys Val Trp Val Trp Thr Trp Asp Asn
                85                  90                  95

Ala Asn Tyr Ser Val Asn Gly Ser Val Ala Asp Arg Lys Gly Asp Arg
            100                 105                 110

-continued

His Tyr Ala Arg Gly Tyr Tyr Arg Ala Gly Ala Asp Arg Asp Gly Gly
            115                 120                 125

Trp Thr Tyr Gly Gly Val Asp Gly Val Thr Gly Lys Asp Ser Thr His
130                 135                 140

Thr Trp Ser Gly Ser Ala Arg Val Ser Lys Asn Gly Lys Thr Asp Val
145                 150                 155                 160

Ala Tyr Arg Asp Lys Asp Gly Asp Val Lys Tyr Asp Ser Arg Ala Ser
                165                 170                 175

Val Gly His Val His Ser Asn Lys Lys Gly Val Lys Thr Gly Asn Lys
            180                 185                 190

Val Lys Ala Asp Gly Lys Asn Tyr Asn Ala Ala Asn Ser Tyr Tyr Asn
        195                 200                 205

Arg Asp Thr Val Asp Ala His Gly Thr Tyr Met Val Gly Asn Ser Ala
    210                 215                 220

Met Asp Arg Asp Ala Lys Cys Thr Ala Asp Gly Tyr Arg Gly Thr Asn
225                 230                 235                 240

Gly Thr Val Val Asn Asn Ser Gly Ala Thr Tyr Gly Asn Val Gly Ala
                245                 250                 255

Arg Ala Lys Asn Lys Ala Thr Trp Ser Ala Asn Cys Val Thr Asp Thr
            260                 265                 270

Arg Tyr Met Asp Gly Lys Tyr Tyr Thr Ser His Arg Ser Thr Ala Thr
        275                 280                 285

Gly Asp Gly Pro Glu Gly Val Tyr Gly Phe Val Gly Asn Gly Ile Arg
    290                 295                 300

Ser Asp Tyr Gln Pro Leu Asn Arg Gly Ser Gly Leu Ala Leu Gly Ser
305                 310                 315                 320

Pro Thr Asn Leu Asn Phe Ala Ala Gly Thr Pro Phe Ala Pro Asp Tyr
                325                 330                 335

Asn Gln His Pro Gly Gln Phe Gln Ala Tyr Ser His Tyr Val Met Pro
            340                 345                 350

Gly Gly Leu Val Gln Ser Phe Ile Asp Thr Ile Gly Thr Lys Asp Asn
        355                 360                 365

Phe Val Arg Gly Gly Thr Leu Gly Pro Thr Val Lys Leu Asn Ile Lys
    370                 375                 380

Gly Asp Ser Ala Thr Val Asp Tyr Asn Tyr Gly Asp Asn Gly Leu Gly
385                 390                 395                 400

Gly Trp Ala Asp Ile Pro Ala Asn Arg Glu Leu Lys Asn Ser Lys Ala
                405                 410                 415

Val Ala Lys

<210> SEQ ID NO 2
<211> LENGTH: 414
<212> TYPE: PRT
<213> ORGANISM: Unknown
<220> FEATURE:
<223> OTHER INFORMATION: Arthrobacter ureafaciens beta-
      fructofuranosidase protein

<400> SEQUENCE: 2

Met Thr Ala Ser Arg Arg Ala Val Gly Ala Gly Ala Gly Ala Ala Gly
1               5                   10                  15

Gly Ala Val Ala Ala Arg Ala Ser Ala Gly Ser Arg Ala Val Tyr His
            20                  25                  30

Met Thr Ser Gly Trp Cys Asp Arg Val Thr Thr His Gly Ala Tyr Tyr
        35                  40                  45

-continued

```
Tyr His Ser Asp Asn Asn Gly Gly Trp Asp His Ala Ser Thr Thr
    50              55              60

Asp Gly Val Ala Thr His His Gly Thr Val Met Arg Asp Val Trp Ser
65              70              75              80

Gly Ser Ala Val Val Gly Thr Ala Asn Thr Ala Gly Gly Ala Gly Ala
                85              90              95

Val Val Ala Ala Thr Thr Asp Gly Val Arg Lys Tyr Tyr Tyr Trp Ser
                100             105             110

Thr Asp Gly Gly Thr Thr Ala Asp Val Val Asn Thr Asp Gly Arg Ala
            115             120             125

Ala Thr Thr Ala Asn Ala Trp Arg Asp Lys His Trp Asp Thr Ala Arg
    130             135             140

Gly Trp Val Cys Val Gly Arg Arg Tyr Ala Ala Tyr Thr Ser Asn Arg
145             150             155             160

Asp Trp Thr Arg Arg Asn Asp Tyr Asn His Ala Gly Gly Cys Asp Thr
                165             170             175

Ala Asp Asp Gly Thr Arg His Trp Val Ala Ala Ser Met Asp Ala Tyr
            180             185             190

Gly Gly Met Thr Tyr Ala Tyr Trp Thr Gly Thr Trp Asp Gly His Ala
        195             200             205

Asp Asp Thr Trp Asp Trp Gly Trp Asp Trp Tyr Ala Ala Val Thr Trp
    210             215             220

Ser Asp Ala Thr Lys Arg Ala Ala Trp Met Asn Asn Trp Lys Tyr Ala
225             230             235             240

Ala Arg Asp Val Thr Asp Ala Ser Asp Gly Tyr Asn Gly Asn Ser Val
                245             250             255

Arg Arg Ala Arg Gly Gly Trp Tyr Thr Ser Thr Val Ala Ala Thr Asn
            260             265             270

Tyr Val Thr Ala Thr Thr Asp Arg Thr Val Asp Gly Ser Ala Val
    275             280             285

Trp Asn Gly Arg Ala Tyr Asp Ala Trp Asp Thr Ala Thr Asn Val Gly
    290             295             300

Ser Val Gly Arg Ser Pro Asp Gly Thr Arg His Thr Asn Ile Gly Lys
305             310             315             320

Tyr Gly Ala Asp Leu Tyr Val Asp Arg Gly Pro Ser Asp Leu Ala Gly
                325             330             335

Tyr Ser Leu Ala Pro Tyr Ser Arg Ala Ala Pro Ile Asp Pro Gly
            340             345             350

Ala Arg Ser Val His Leu Arg Ile Leu Val Asp Thr Gln Ser Val Glu
    355             360             365

Val Phe Val Asn Ala Gly His Thr Val Leu Ser Gln Gln Val His Phe
    370             375             380

Ala Glu Gly Asp Thr Gly Ile Ser Leu Tyr Thr Asp Gly Gly Pro Ala
385             390             395             400

His Phe Thr Gly Ile Val Val Arg Glu Ile Gly Gln Ala Ile
                405             410
```

METHOD FOR PREPARING TRANSFRUCTOSYLATED STEVIOL GLYCOSIDE USING MICROORGANISM OF GENUS ARTHROBACTER

SEQUENCE LISTING SUBMISSION VIA EFS-WEB

A computer readable text file, entitled "SequenceListing.txt," created on or about Apr. 27, 2020 with a file size of about 7 kb contains the sequence listing for this application and is hereby incorporated by reference in its entirety.

TECHNICAL FIELD

The present disclosure relates to a method for preparing a transfructosylated steviol glycoside using microorganisms of the genus *Arthrobacter*.

BACKGROUND ART

As the World Health Organization (WHO) recommends lowering the amount of daily sugar intake due to concerns about disease (obesity) caused by sugar consumption, various policies aimed at reducing the amount of sugar intake are actively being discussed by the governments of developed countries. Therefore, as the need for developing various alternative sweeteners is increasing in the market, alternative sweeteners are continuously being developed and commercialized. As alternative sweeteners, these are the subject of continuous variation in the form of synthetic high-intensity sweeteners (e.g., Saccharin, Aspartame, Sucralose, etc.), synthetic sugar alcohols (e.g., Maltitol and Xylitol), and high-intensity sweeteners (e.g., Rebaudioside A and Liquorice). Nevertheless, due to concerns over the safety of synthetic sweeteners, customers' need for natural sweeteners has been steadily increasing; however, because of limitations to peculiar flavor properties of natural sweeteners (i.e., off-smell and off-flavor), natural sweeteners cannot fully replace existing low-calorie and zero-calorie products based on synthetic sweeteners.

A natural high-intensity sweetener that has received considerable attention in recent years is *Stevia* extracted from the leaves of *Stevia rebaudiana* Bertoni. *Stevia* is a natural material, the sweetness of which is 200 to 300 times that of sugar. Further, *Stevia* consists of Stevioside, Rebaudioside A, B, C, D, E, and M, Dulcoside A, Rubusoside, etc. Furthermore, *Stevia* has a potential use as an alternative sweetener because it has been reported that it does not generate calories, it is positive for blood glucose and insulin levels, and it has no side effects on the human body; however, *Stevia* has a bitter taste, which presents a limitation in use.

Thus far, there have been three methods to improve the sweetness of *Stevia*: (1) a method of mixing with a saccharide sweetener, an amino acid, or an amino acid salt, (2) a physical method of including a material such as cyclodextrin; and (3) a method of transferring glucose using an enzyme. As the method of transferring saccharide using an enzyme, a method of transferring 1 to 12 glucose molecules to a steviol glycoside using CGTase is widely used in the art (Korean Patent Application No. 10-1991-0020769). However, such method has a disadvantage in that all glucose transferred to the steviol glycoside is degraded by intestinal microorganisms, increasing calories. Therefore, there is a need for a novel method of preparing a steviol glycoside wherein a saccharide other than glucose is transferred.

DISCLOSURE

Technical Problem

The present inventors have completed the present disclosure by discovering that there is a transfructosylating activity to a steviol glycoside by a β-bond using four microorganisms of the genus *Arthrobacter*.

Technical Solution

An object of the present disclosure is to provide a method for preparing a transfructosylated steviol glycoside using one or more microorganisms of the genus *Arthrobacter* selected from the group consisting of *Arthrobacter globiformis*, *Arthrobacter crystallopoietes*, *Arthrobacter ureafaciens*, and *Arthrobacter aurescens*; a culture thereof; a supernatant of the culture; an extract of the culture; and a lysate of the microorganisms.

Another object of the present disclosure is to provide a transfructosylated steviol glycoside prepared according to the preparation method above.

Still another object of the present disclosure is to provide a composition for producing the transfructosylated steviol glycoside, comprising one or more microorganisms of the genus *Arthrobacter* selected from the group consisting of *Arthrobacter globiformis*, *Arthrobacter crystallopoietes*, *Arthrobacter ureafaciens*, and *Arthrobacter aurescens*; a culture thereof; a supernatant of the culture; an extract of the culture; and a lysate of the microorganisms.

Advantageous Effects

The method of the present disclosure for preparing a transfructosylated steviol glycoside can specifically produce a transfructosylated steviol glycoside by using one or more microorganisms of the genus *Arthrobacter* selected from the group consisting of *Arthrobacter globiformis*, *Arthrobacter crystallopoietes*, *Arthrobacter ureafaciens*, and *Arthrobacter aurescens*; a culture thereof; a supernatant of the culture; an extract of the culture; and a lysate of the microorganisms. The transfructosylated steviol glycoside according to the present disclosure is a material for a high-intensity sweetener having an improved bitter taste and of which the caloric content is not high compared to a known transglucosylated steviol glycoside, and can thereby be used in various fields.

BRIEF DESCRIPTION OF DRAWINGS

FIGS. 1 to 9 show HPLC results of the transfructosylated steviol glycosides prepared using the microorganisms of the genus *Arthrobacter*, cultures thereof, supernatants of the cultures, extracts of the cultures, and lysates of the microorganisms.

FIG. 10 shows HPLC/MS results of the transfructosylated steviol glycosides prepared using the microorganisms of the genus *Arthrobacter*, cultures thereof, supernatants of the cultures, extracts of the cultures, and lysates of the microorganisms.

FIG. 11 is graphs showing the conversion rate of the transfructosylated steviol glycosides (Stevioside and Rebaudioside A) according to temperature.

FIG. 12 is graphs showing the conversion rate of the transfructosylated steviol glycosides (Stevioside and Rebaudioside A) according to pH.

FIG. 13 is graphs showing the conversion rate of the transfructosylated steviol glycoside according to concentrations of the steviol glycosides (Stevioside and Rebaudioside A).

DETAILED DESCRIPTION OF PREFERRED EMBODIMENTS

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the objects of the present disclosure, an aspect of the present disclosure provides a method for preparing a transfructosylated steviol glycoside, comprising preparing a transfructosylated steviol glycoside by reacting a steviol glycoside with sugar in the presence of four microorganisms of the genus *Arthrobacter*, a culture thereof, a supernatant of the culture, an extract of the culture, and a lysate of the microorganisms.

As used herein, the term "steviol glycoside" refers to a natural sweetener having Chemical Formula 1. The steviol glycoside is advantageous in that it has fewer calories compared with sugar, and that the sweetness thereof is about 200 to 300 times of that of sugar; but is disadvantageous in that it is accompanied by a unique astringent or bitter taste. Therefore, efforts have been made to improve the sweetness of the steviol glycoside.

[Chemical Formula 1]

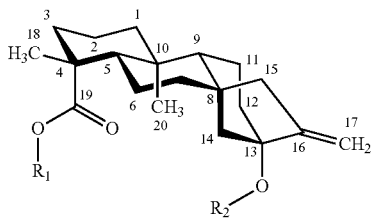

In Chemical Formula 1, at $R_1$, hydrogen (H) may be bound, or 1 to 3 glucose molecules may be bound via a β-bond; and at $R_2$, any one of glucose, xylose, and rhamnose may be bound, and 0 to 2 glucose molecules may be bound thereto via a β-bond, but these are not limited thereto.

The α-/β-glycosidic bonds are distinguished by the anomeric position and relative stereochemistry (R-type or S-type) of the stereocenter which is the most distant from the 1-carbon of a monosaccharide. In general, the α-glycosidic bond is formed when two carbons have the same stereochemistry, whereas the β-glycosidic bond occurs when two carbons have different stereochemistry. The present inventors have found for the first time that one or more microorganisms of the genus *Arthrobacter* selected from the group consisting of *Arthrobacter globiformis, Arthrobacter crystallopoietes, Arthrobacter ureafaciens*, and *Arthrobacter aurescens*, a culture thereof, a supernatant of the culture, an extract of the culture, and a lysate of the microorganisms decompose sugar into fructose using the sugar as a substrate, and selectively link 1 to 3 fructose molecules to a steviol glycoside by a β-bond. In addition, the present inventors have first discovered that the four *Arthrobacter*-derived microorganisms of the present disclosure, a culture thereof, a supernatant of the culture, an extract of the culture, and a lysate of the microorganisms are advantageous in that they have an excellent conversion rate into a transfructosylated steviol glycoside, and that the sweetness thereof is remarkably increased compared to an existing steviol glycoside.

As used herein, the term "transfructosylated steviol glycoside" may refer to a steviol glycoside having the form in which, by using sugar and a steviol glycoside as substrates, 1 to 3 fructose molecules are added directly to a 19-OH site of the steviol glycoside or to the glucose, which is conjugated thereto, via a β-bond by one or more microorganisms of the genus *Arthrobacter* selected from the group consisting of *Arthrobacter globiformis, Arthrobacter crystallopoietes, Arthrobacter ureafaciens*, and *Arthrobacter aurescens*; a culture thereof; a supernatant of the culture; an extract of the culture; and a lysate of the microorganisms. More specifically, the transfructosylated steviol glycoside may be in the form wherein 1 to 3 fructose molecules are added directly to a 19-OH site of the steviol glycoside or to the glucose, which is conjugated thereto, by a β-(2,6) bond, but is not limited thereto.

Each step of the method for preparing the transfructosylated steviol glycoside will be described in detail. First, in the method, one or more microorganisms of the genus *Arthrobacter* selected from the group consisting of *Arthrobacter globiformis, Arthrobacter crystallopoietes, Arthrobacter ureafaciens*, and *Arthrobacter aurescens*; a culture thereof; an extract of the culture; and a lysate of the microorganisms may be prepared.

In the next step of the method for preparing the transfructosylated steviol glycoside, sugar may be reacted with a steviol glycoside in the presence of the microorganisms of the genus *Arthrobacter*, a culture thereof, a supernatant of the culture, an extract of the culture, and a lysate of the microorganisms.

Herein, the steviol glycoside may be one or more selected from the group consisting of Stevioside, Rubusoside, Dulcoside A, Rebaudioside A, Rebaudioside C, Rebaudioside D, Rebaudioside E, Rebaudioside F, and Rebaudioside M, but is not limited thereto.

The step of reacting sugar with the steviol glycoside may be carried out at a pH of 1 to 10 at a temperature of 1° C. to 80° C., more specifically at a pH of 2 to 9 at a temperature of 5° C. to 70° C., and most specifically at a pH of 3 to 8 at a temperature of 10° C. to 60° C., but the pH and temperature are not limited thereto.

In order to achieve the objects of the present disclosure, another aspect of the present disclosure provides a transfructosylated steviol glycoside prepared by the preparation method above. The transfructosylated steviol glycoside may be in the form in which 1 to 3 fructose molecules are added directly to a 19-OH site of the steviol glycoside or to the glucose, which is conjugated thereto, via a β-bond, and more specifically may be in the form in which 1 to 3 fructose molecules are added directly to a 19-OH site of the steviol glycoside or to the glucose, which is conjugated thereto, via a β-(2,6) bond, but is not limited thereto.

The microorganisms of the genus *Arthrobacter*, culture thereof, supernatant of the culture, extract of the culture, and lysate of the microorganisms may have a conversion rate from the steviol glycoside to the transfructosylated steviol glycoside of 30% to 70%, but the conversion rate is not limited thereto. Specifically, the conversion rate to the transfructosylated Stevioside of the present disclosure is higher than that of other known microbial-derived enzymes. More specifically, the conversion rate to the transfructosylated Stevioside may be 10% to 80%, and specifically may be 10% to 80%, 20% to 75%, or 30% to 70%, but the conversion rate is not limited thereto.

Additionally, the microorganisms of the genus *Arthrobacter*, culture thereof, supernatant of the culture, extract of the culture, and lysate of the microorganisms may be 0.01% (w/w) to 16% (w/w) in a reaction solution, and more specifically may be 0.05% (w/w) to 8% (w/w), 0.1% (w/w) to 6% (w/w), 0.2% (w/w) to 4% (w/w), 0.4% (w/w) to 3% (w/w), 0.6% (w/w) to 2% (w/w), 0.8% (w/w) to 1.5% (w/w), or 1% (w/w), but it is not limited thereto.

More specifically, the transfructosylated steviol glycoside prepared according to the method above may be one or more selected from the group consisting of transfructosylated Stevioside, transfructosylated Rubusoside, transfructosylated Dulcoside A, transfructosylated Rebaudioside A, transfructosylated Rebaudioside C, transfructosylated Rebaudioside D, transfructosylated Rebaudioside E, transfructosylated Rebaudioside F, and transfructosylated Rebaudioside M, but is not limited thereto.

Still another aspect of the present disclosure provides a composition for producing the transfructosylated steviol glycoside, comprising one or more microorganisms of the genus *Arthrobacter* selected from the group consisting of *Arthrobacter globiformis*, *Arthrobacter crystallopoietes*, *Arthrobacter ureafaciens*, and *Arthrobacter aurescens*; a culture thereof; a supernatant of the culture; an extract of the culture; and a lysate of the microorganisms.

MODE FOR CARRYING OUT THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation Method of Crude Enzyme Liquid of Microorganisms of the Genus *Arthrobacter*

In a nutrient medium containing a yeast extract and corn steep liquor as nitrogen sources and sugar as a carbon source, 10 microorganisms of the genus *Arthrobacter* (i.e., *A. atorocyaneus* KCCM 41106, *A. crystallopoietes* KCCM 41107, *A. sulfureus* KCCM 12457, *A. oxydans* KCCM 11369, *A. globiformis* KCCM 40830, *A. globiformis* KCCM 40829, *A. globiformis* KCCM 40800, *A. ureafaciens* KCCM 40801, *A. ureafaciens* KCCM 40828, and *A. aurescens* KCCM 41109) were cultured at 30° C. for 24 hours to 48 hours. The cultures were centrifuged to separate the cells and supernatants, and then the supernatants were only used to prepare crude enzyme liquids. The sugar hydrolytic activity of the 10 microorganisms of the genus *Arthrobacter* was confirmed by a DNS method.

Example 2: Evaluation of Conversion from Steviol Glycoside to Transfructosylated Steviol Glycoside Steviol glycosides and sugar were dissolved in a 0.05 M acetate buffer solution, and the crude enzyme liquids of the 9 microorganisms of the genus *Arthrobacter*, which had been prepared in Example 1, were added thereto, followed by reacting at 40° C. for 24 hours. After the reaction, the resultants were inactivated at 100° C., and then the production of transfructosylated steviol glycosides was confirmed by HPLC.

Table 1 below shows the sugar hydrolytic activity and the transfructosylation activity to steviol glycoside of the crude enzyme liquids derived from the 10 microorganisms of the genus *Arthrobacter*; and FIGS. 1a and 1b show the HPLC chromatographic results of the transfructosylated steviol glycosides which were prepared using the crude enzyme liquids derived from the microorganisms of the genus *Arthrobacter*.

TABLE 1

| Strain Name | Sugar Hydrolysis | Transfructosylated Steviol Glycoside |
|---|---|---|
| *Arthrobacter atorocyaneus* KCCM 41106 | ◯ | X |
| *Arthrobacter crystallopoietes* KCCM 41107 | ◯ | ◯ |
| *Arthrobacter sulfureus* KCCM 12457 | ◯ | X |
| *Arthrobacter oxydans* KCCM 11369 | ◯ | X |
| *Arthrobacter globiformis* KCCM 40830 | ◯ | ◯ |
| *Arthrobacter globiformis* KCCM 40829 | ◯ | ◯ |
| *Arthrobacter globiformis* KCCM 40800 | ◯ | ◯ |
| *Arthrobacter ureafaciens* KCCM 40801 | ◯ | ◯ |
| *Arthrobacter ureafaciens* KCCM 40828 | ◯ | ◯ |
| *Arthrobacter aurescens* KCCM 41109 | ◯ | ◯ |

Based on Table 1 above, the four microorganisms of the genus *Arthrobacter* having the transfructosylating activity to the steviol glycosides (i.e., *A. crystallopoietes*, *A. globiformis*, *A. ureafaciens*, and *A. aurescens*) were selected. FIGS. 1 to 9 show the production of the transfructosylated steviol glycosides by HPLC analysis of a reaction solution obtained by reacting the crude enzyme liquids of the 10 microorganisms of the genus *Arthrobacter* with the steviol glycosides. Herein, the steviol glycosides are Stevioside, Rubusoside, Dulcoside A, and Rebaudiosides A/C/D/E/F/M, and whether they produced transfructosylated Stevioside, transfructosylated Rubusoside, transfructosylated Dulcoside A, and transfructosylated Rebaudiosides A/C/D/E/F/M was confirmed by HPLC.

As a result, of the 10 microorganisms of the genus *Arthrobacter*, only 7 microorganisms produced the transfructosylated steviol glycosides. Such result implies that only some specific microorganisms of the genus *Arthrobacter* have the activity of specifically transferring fructose to a steviol glycoside. The molecular weights of the transfructosylated steviol glycosides were determined by carrying out HPLC/MS analysis to confirm the fructose polymerization degree of the transfructosylated steviol glycosides.

FIGS. 10a to 10e show the results of the HPLC/MS analysis for the transfructosylated steviol glycosides prepared using the *Arthrobacter globiformis*-derived microorganisms.

As a result, it was confirmed that in the transfructosylated steviol glycosides prepared using the enzymes derived from *Arthrobacter globiformis*, 1 to 3 fructose molecules were randomly transferred to the steviol glycosides.

Example 3: Effect of Temperature on Synthesis of Transfructosylated Steviol Glycoside In the production of the transfructosylated steviol glycosides by the crude enzyme liquids derived from *Arthrobacter globiformis*, the effect of temperature was evaluated. Steviol glycosides and sugar were dissolved in an acetic acid buffer solution (pH 5.0), and the crude enzyme liquids were added thereto, followed by reacting at 10° C. to 60° C. for 24 hours. After the reaction, the production of the transfructosylated steviol glycosides in the reaction solutions was analyzed by HPLC.

FIG. 11 is graphs showing the conversion rate of the transfructosylated steviol glycosides (Stevioside and Rebaudioside A) according to temperature.

As a result, it was confirmed that the conversion rate to the transfructosylated steviol glycosides by the crude enzyme liquids of *Arthrobacter globiformis* was as high as 50% to 70% at 20° C. to 40° C.

Example 4: Effect of pH on Synthesis of Transfructosylated Steviol Glycoside In the production of the transfructosylated steviol glycosides by the crude enzyme liquids derived from *Arthrobacter globiformis*, the effect of pH was evaluated. Steviol glycosides and sugar were dissolved in an acetic acid buffer solution (pH 3.0 to pH 5.0), a phosphate buffer solution (pH 6.0), and a Tris buffer solution (pH 7.0 to pH 8.0). Thereafter, the crude enzyme liquids were added thereto, and the reaction was carried out at pH 3 to pH 8 for 24 hours. After the reaction, the production of the transfructosylated steviol glycosides was analyzed by HPLC.

FIG. 12 is graphs showing the conversion rate of the transfructosylated steviol glycosides (Stevioside and Rebaudioside A) according to pH.

As a result, it was confirmed that the conversion rate to the transfructosylated steviol glycosides by the crude enzyme liquids of *Arthrobacter globiformis* was high at pH 4.0 to pH 7.0, and particularly, was the highest at pH 5.0.

Example 5: Analysis of Transfructosylated Steviol Glycoside According to Concentration of Steviol Glycoside The production of the transfructosylated steviol glycosides according to the concentrations of the steviol glycosides by the crude enzyme liquids of *Arthrobacter globiformis* was evaluated. Sugar and steviol glycosides (Stevioside and Rebaudioside A) were dissolved in an acetic acid buffer solution (pH 5.0), and the reaction was carried out at 40° C. for 24 hours. The reaction was carried out under conditions of a sugar concentration of 0.75 M and a final enzyme concentration of 50 U/mL. After the reaction, the production of the transfructosylated steviol glycosides was analyzed by HPLC.

FIG. 13 is graphs showing the conversion rate of the transfructosylated steviol glycosides according to the concentrations of the Stevioside.

As a result, it was confirmed that the conversion rate to the transfructosylated steviol glycosides by the crude enzyme liquids of *Arthrobacter globiformis* was high at 0.4% (w/w) to 4% (w/w), and particularly, was the highest at 1% (w/w).

FIG. 13 is a graph showing the synthetic conversion rate of transfructosylated Rebaudioside A according to the concentrations of Rebaudioside A. As a result, it was confirmed that the conversion rate to transfructosylated Rebaudioside A by the crude enzyme liquids of *Arthrobacter globiformis* was high at 0.5% (w/w) to 2% (w/w), and particularly, was the highest at 1% (w/w).

Example 6: Nuclear Magnetic Resonance (NMR) Analysis of Transfructosylated Steviol Glycoside Sugar and steviol glycosides were dissolved in an acetic acid buffer solution (pH 5.0), and then the crude enzyme liquids were added thereto, followed by reacting at 40° C. for 24 hours. The reaction solutions were inactivated at 100° C., and then impurities were removed using a 0.45 μm filter. Each of the steviol glycosides (Stevioside and Rebaudioside A), in which one fructose was transferred, was purely separated using an HP20 resin. The bonding structures of the separated transfructosylated Stevioside and transfructosylated Rebaudioside A were analyzed by $^1H/^{13}C$ NMR, homonuclear correlation spectroscopy (COSY), total correlation spectroscopy (TOCSY), heteronuclear single-quantum coherence (HSQC), and heteronuclear multiple-bond correlation (HMBC). In addition, the results thereof ($^1H/^{13}C$ NMR, COSY, and HMBC) are shown in Tables 2 and 3.

Additionally, as a result of identifying the structures of the transfructosylated Stevioside and transfructosylated Rebaudioside A, it was confirmed that these were novel compounds as the transfructosylated Stevioside has a structure of 13-[(2-O-β-D-glucopyranosyl-α-D-glucopyranosyl)oxy] kaur-16-en-18-oic acid 6-O-β-D-fructofuranose-β-D-glucopyranosyl ester and the transfructosylated Rebaudioside A has a structure of 13-[(2-O-β-D-glucopyranosyl-3-O-β-D-glucopyranosyl-β-D-glucopyranosyl)oxy]ent-kaur-16-en-19-oic acid 6-O-β-D-fructofuranose-β-D-glucopyranosyl ester.

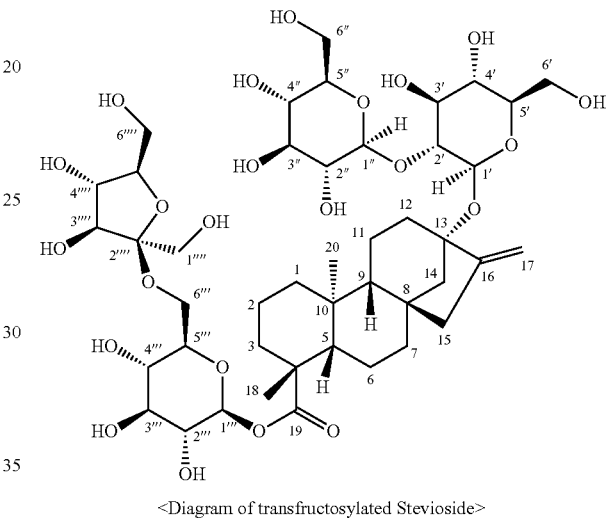

<Diagram of transfructosylated Stevioside>

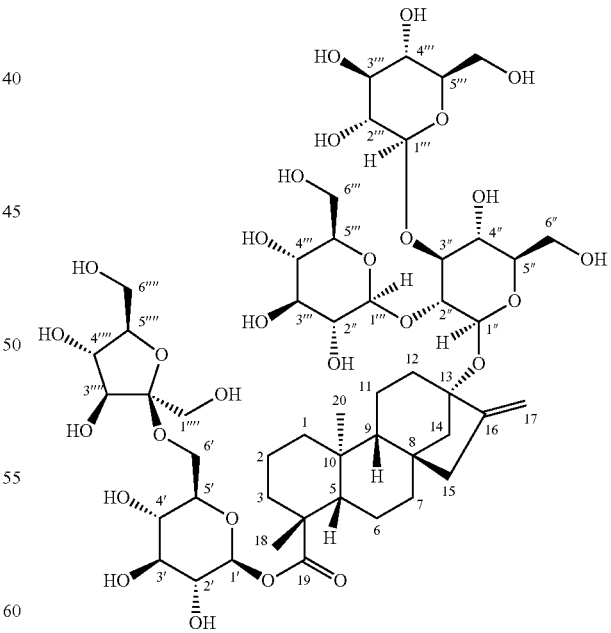

<Diagram of transfructosylated Rebaudioside A>

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

TABLE 2

| Position | $\delta_H$ mult. (J in Hz) | $\delta_C$ mult. | HMBC Correlation | COSY correlation | Key ROESY correlation |
|---|---|---|---|---|---|
| 1 | 0.77 br m/1.81 br m | 40.3 $CH_2$ | | 1.81/0.77 | |
| 2 | 1.37 br m/1.78 br m | 18.7 $CH_2$ | | 1.78/1.37 | |
| 3 | 1.00 br m/2.09 br m | 37.5 $CH_2$ | 56.8/40.3, 43.8 | 1.78, 2.09/1.00 | /1.18 |
| 4 | | 43.8 C | | | |
| 5 | 1.07 br s | 56.8 CH | 21.4, 28.0, 39.3, 40.9, 43.8, 178.6 | 1.80 | |
| 6 | 1.80 br m | 21.4 $CH_2$ | | 1.07 | 3.40 |
| 7 | 1.35 br m/1.52 br m | 40.9 $CH_2$ | /56.8, 42.1 | 1.52/1.35 | 1.18 |
| 8 | | 42.1 C | | | |
| 9 | 0.90 br s | 53.4 CH | 20.3, 36.1, 39.3, 42.1, 44.2, 47.0 | 1.55 | |
| 10 | | 39.3 C | | | |
| 11 | 1.55 br m/1.75 br m | 20.3 $CH_2$ | 39.3, 53.4/39.3, 42.1, 86.9 | 1.90, 1.75/1.55 | |
| 12 | 1.47 br m/1.90 br m | 36.1 $CH_2$ | | 1.90/1.47 | |
| 13 | | 86.9 C | | | |
| 14 | 1.40 br d (10.0) 2.11 br m | 44.2 | 36.1, 42.1, 53.4, 86.9 36.1, 47.0 | 2.11 1.40 | 0.83, 3.22 |
| 15 | 1.96 br d (17.0) 2.12 br d (17.0) | 47.0 $CH_2$ | 42.1, 44.2, 53.4, 86.9, 153.0 42.1, 53.4, 86.9, 104.8, 153.0 | 2.12 1.96 | |
| 16 | | 153.0 C | | | |
| 17 | 4.84 br s/5.08 br s | 104.8 $CH_2$ | | 2.12/1.96, 2.12 | /3.22, 3.31 |
| 18 | 1.18 s | 28.0 $CH_3$ | 37.5, 43.8, 56.8, 178.6 | | 1.80, 2.09, 3.40, 3.45, 3.65, 4.01, 5.34 |
| 19 | | 178.6 C | | | |
| 20 | 0.83 s | 15.1 $CH_3$ | 39.3, 40.3, 53.4, 56.8 | | 1.78, 2.11, 3.22, 3.25, 5.34 |
| 1' | 4.65 br d (7.5) | 95.8 CH | 86.9 | 3.46 | 3.26, 3.57 |
| 2' | 3.46 br m | 80.6 CH | 75.7, 95.8, 103.1 | 3.57, 4.65 | |
| 3' | 3.57 br m | 75.6 CH | 69.6, 80.6, 95.8w | 3.33, 3.46 | |
| 4' | 3.33 br m | 69.6 CH | 60.7, 75.6 | 3.26, 3.57 | |
| 5' | 3.26 br m | 75.6 CH | 69.6 | 3.33, 3.62 | |
| 6' | 3.62 br m/3.76 br m | 60.7 $CH_2$ | | 3.26, 3.76/3.62 | |
| 1" | 4.62 d (7.5) | 103.1 CH | 80.6 | 3.22 | 3.46, 3.41, 3.31, 0.83 |
| 2" | 3.22 t (7.5) | 74.3 CH | 75.6, 103.1 | 3.41, 4.62 | |
| 3" | 3.41 br m | 75.6 CH | 69.8, 74.3 | 3.22, 3.25 | |
| 4" | 3.25 br m | 69.8 CH | 61.2, 75.6, 76.3 | 3.31, 3.41 | 0.83 |
| 5" | 3.31 br m | 76.3 CH | 69.8 | 3.25, 3.59 | |
| 6" | 3.59 br m/3.78 br m | 61.2 $CH_2$ | | 3.31, 3.78/3.59 | |
| 1''' | 5.34 d (8.0) | 94.1 CH | 178.6, 75.8 | 3.40 | 0.83, 1.18, 3.45, 3.54 |
| 2''' | 3.40 t (8.0) | 71.9 CH | 94.1, 76.0 | 3.45, 5.34 | 1.18 |
| 3''' | 3.45 br m | 76.0 CH | 68.8 | 3.40 | 1.18 |
| 4''' | 3.45 br m | 68.8 CH | 60.1, 71.9, 76.0 | | |
| 5''' | 3.54 br m | 75.6 CH | 68.8 | 3.65 | |
| 6''' | 3.65 br m 3.87 br m | 60.1 $CH_2$ | 75.6, 103.6 68.8, 75.6, 103.6 | 3.54 | /3.54, 3.65 |
| 1'''' | 3.55 br m/3.63 br m | 60.0 $CH_2$ | 77.0, 103.6, | | |
| 2'''' | | 103.6 CH | | | |
| 3'''' | 4.07 d (8.5) | 77.0 CH | 60.0, 74.5, 103.6 | 4.01 | 3.55, 3.63, 3.76, |
| 4'''' | 4.01 t (8.5) | 74.5 CH | 62.5, 77.0, 81.4 | 3.76, 4.07 | 1.18, 3.53, 3.65, 3.76 |
| 5'''' | 3.76 | 81.4 CH | 74.5, 103.6 | 3.53, 4.01 | |
| 6'''' | 3.53 br m/3.65 br m | 62.5 $CH_2$ | 74.5, 81.4/74.5 | 3.65, 3.76/3.53 | |

TABLE 3

| No. | $d_H$ mult. (J in Hz) | $d_C$ mult | HMBC Correlation | COSY corr. | Key ROESY corr. |
|---|---|---|---|---|---|
| 1 | 0.76 br m | 40.3 $CH_2$ | 15.0 | 1.37''', 1.78, 1.81 | |
| 2 | 1.37 br m | 18.7 $CH_2$ | | 1.78 | |
| 3 | 0.99 br m | 37.6 $CH_2$ | | 1.78, 2.08 | |
| 4 | | 43.8 C | | | |
| 5 | 1.05 br m | 56.9 CH | 15.0, 21.4, 28.0, 39.3, 40.9, | 1.81 | |
| 6 | 1.81 br m | 21.4 $CH_2$ | | 1.35 | 3.40 |
| 7 | 1.35 br m | 40.9 $CH_2$ | | 1.53 | |
| 8 | | 42.0 C | | | |
| 9 | 0.89 br s | 53.5 CH | 15.0, 20.3, 36.3, 39.3, 42.0, | 1.54 | |
| 10 | | 39.3 C | | | |
| 11 | 1.54 br m | 20.3 $CH_2$ | 42.0, 53.5, 87.1 | 1.75, 1.89 | |
| 12 | 1.46 br m | 36.3 $CH_2$ | | 1.89 | |
| 13 | | 87.1 C | | | |

TABLE 3-continued

| No. | $d_H$ mult. (J in Hz) | $d_C$ mult | HMBC Correlation | COSY corr. | Key ROESY corr. |
|---|---|---|---|---|---|
| 14 | 1.43 br m | 44.0 | 36.3, 42.0, 53.5, 87.1, | 2.09 | |
| 15 | 1.95 br d (16.0) | 47.1 $CH_2$ | 44.0 | 2.14 | |
| 16 | | 152.9 C | | | |
| 17 | 4.85 br s | 104.8 $CH_2$ | 47.1, 87.1, 152.9 | 2.14 | |
| 18 | 1.17 s | 28.0 $CH_3$ | 37.6, 43.8, 56.9, 178.4 | | 1.81, 3.40 |
| 19 | | 178.4 C | | | |
| 20 | 0.83 s | 15.0 $CH_3$ | 39.3, 40.3, 53.5, 56.9 | | 3.17, 3.41, 5.37 |
| 1' | 5.37 d (8.0) | 94.1 CH | 75.2, 178.4 | 3.40 | 3.40, 3.47, 3.66 |
| 2' | 3.40 br m | 71.9 CH | 76.3, 94.1 | 3.47, 5.37 | 1.17, 1.81 |
| 3' | 3.47 br m | 76.3 CH | 68.9, 71.9, | 3.40 | |
| 4' | 3.48 br m | 68.9 CH | 65.2, 75.2, 76.3 | 3.66 | |
| 5' | 3.66 br m | 75.2 CH | | 3.48, 3.64 | |
| 6' | 3.64 br m | 65.2 $CH_2$ | 97.8 | 3.87 | |
| 1" | 4.66 ovlp solv. | 95.9 CH | 75.2, 87.1 | 3.65 | |
| 2" | 3.65 br m | 78.6 CH | 85.1, 95.9, 102.11 | 4.66 | |
| 3" | 3.80 br m | 85.1 CH | 68.5, 78.6, 102.20 | 3.42 | 3.30, 3.70, |
| 4" | 3.42 br m | 68.5 CH | 60.8, 75.2, 85.1 | 3.29~3.33, 3.80 | |
| 5" | 3.30 br m | 75.2 CH | | 3.64 | 3.80 |
| 6" | 3.64 br m | 60.8 $CH_2$ | | 3.30, 3.78 | |
| 1''' | 4.77 br d (8.0) | 102.1 CH | 75,9, 76.5, 78.6 | 3.17 | 3.31, 3.37, 3.65 |
| 2''' | 3.17 br m | 74.1 CH | 75.9, 120.1 | 3.37, 4.77 | 1.46, 2.09 |
| 3''' | 3.37 br m | 75.9 CH | 70.2, 74.1 | 3.17 | |
| 4''' | 3.18 br m | 70.3 CH | 61.5, 75.9, 76.5 | 3.31 | |
| 5''' | 3.31 br m | 76.5 CH | 61.5 | 3.18, 3.55 | |
| 6''' | 3.55 br m* | 61.5 $CH_2$ | 76.5 | 3.80 | |
| 1'''' | 4.70 ovlp solv. | 102.2 CH | 75.8, 76.1, 85.1, | 3.29 | |
| 2'''' | 3.29 br m | 73.3 CH | 75.8, 102.2 | 3.42, 4.70 | |
| 3'''' | 3.42 br m | 75.8 CH | 69.5, 73.3 | 3.29~3.33 | |
| 4'''' | 3.33 br m | 69.5 CH | 61.6, 75.8, 76.1 | 3.42 | |
| 5'''' | 3.41 br m | 76.1 CH | | 3.63 | |
| 6'''' | 3.63 br m | 60.6 $CH_2$ | 76.3 | 3.41, 3.83 | |
| 1''''' | 4.83 br d (3.0) | 97.8 CH | 65.2, 71.7, 73.1 | 3.45 | 3.45, 3.64 |
| 2''''' | 3.45 br m | 71.4 CH | 97.8, | 3.63, 4.83 | |
| 3''''' | 3.63 br m | 73.1 CH | 69.3, 71.4 | 3.34, 3.45 | |
| 4''''' | 3.34 br m | 69.3 CH | 60.3, 71.7, 73.1 | 3.59, 3.63 | |
| 5''''' | 3.59 br m | 71.7 CH | | 3.34, 3.68 | |
| 6''''' | 3.68 br m* | 60.3 $CH_2$ | | 3.59, 3.71 | |

The invention claimed is:

1. A method for preparing a transfructosylated steviol glycoside using one or more microorganisms of the genus Arthrobacter selected from the group consisting of *Arthrobacter globiformis*, *Arthrobacter crystallopoietes*, *Arthrobacter ureafaciens*, and *Arthrobacter aurescens*; a culture thereof; a supernatant of the culture; an extract of the culture; and a lysate of the microorganisms.

2. The method according to claim 1, wherein the method comprises reacting a steviol glycoside with sugar in the microorganisms of the genus Arthrobacter, the culture thereof, the supernatant of the culture, the extract of the culture, and the lysate of the microorganisms.

3. The method according to claim 2, wherein the steviol glycoside is one or more selected from the group consisting of Stevioside, Rubusoside, Dulcoside A, Rebaudioside A, Rebaudioside C, Rebaudioside D, Rebaudioside E, Rebaudioside F, and Rebaudioside M.

4. The method according to claim 2, wherein reacting the steviol glycoside with the sugar is carried out at a pH of 3 to 8 at a temperature of 10° C. to 60° C.

5. The method according to claim 1, wherein the transfructosylated steviol glycoside comprises 1 to 3 fructose molecules.

6. The method according to claim 1, wherein the transfructosylated steviol glycoside is a steviol glycoside in which fructose is added by linking directly to a 19-OH site of the steviol glycoside or through glucose conjugated thereto by a β-(2,6) bond.

7. The method according to claim 1, wherein said one or more microorganisms comprises *Arthrobacter globiformis*.

8. The method according to claim 1, wherein said one or more microorganisms comprises *Arthrobacter crystallopoietes*.

9. The method according to claim 1, wherein said one or more microorganisms comprises *Arthrobacter ureafaciens*.

10. The method according to claim 1, wherein said one or more microorganisms comprises *Arthrobacter aurescens*.

11. The method according to claim 1, wherein the steviol glycoside comprises Rebaudioside A.

12. The method according to claim 1, wherein the steviol glycoside comprises Rebaudioside D.

13. The method according to claim 1, wherein the steviol glycoside comprises Rebaudioside M.

* * * * *